(12) United States Patent
Amini

(10) Patent No.: US 12,385,009 B2
(45) Date of Patent: Aug. 12, 2025

(54) METHODS AND COMPOSITIONS FOR GENERATING OLIGODENDROCYTE PROGENITOR CELLS

(71) Applicant: Trailhead Biosystems Inc., Cleveland, OH (US)

(72) Inventor: Nooshin Amini, Cleveland, OH (US)

(73) Assignee: Trailhead Biosystems Inc., Cleveland, OH (US)

(*) Notice: Subject to any disclaimer, the term of this patent is extended or adjusted under 35 U.S.C. 154(b) by 326 days.

(21) Appl. No.: 17/587,552

(22) Filed: Jan. 28, 2022

(65) Prior Publication Data

US 2022/0315891 A1  Oct. 6, 2022

Related U.S. Application Data

(60) Provisional application No. 63/168,065, filed on Mar. 30, 2021.

(51) Int. Cl.
C12N 5/00 (2006.01)
C12N 5/079 (2010.01)

(52) U.S. Cl.
CPC ...... *C12N 5/0622* (2013.01); *C12N 2501/155* (2013.01); *C12N 2501/385* (2013.01); *C12N 2501/41* (2013.01); *C12N 2501/415* (2013.01); *C12N 2501/727* (2013.01); *C12N 2506/02* (2013.01); *C12N 2506/45* (2013.01); *C12N 2533/50* (2013.01)

(58) Field of Classification Search
CPC .. C12N 5/0622; C12N 2501/155; C12N 5/00; C12N 5/06; C12N 5/0018
See application file for complete search history.

(56) References Cited

U.S. PATENT DOCUMENTS

| | | |
|---|---|---|
| 8,227,247 B2 | 7/2012 | Zhang et al. |
| 8,633,025 B2 | 1/2014 | Vanderhaeghen et al. |
| 10,100,279 B2 | 10/2018 | Nicholas et al. |
| 10,301,592 B2 | 5/2019 | Fossati et al. |
| 10,828,335 B2 | 11/2020 | George et al. |
| 2015/0361393 A1 | 12/2015 | Nicholas et al. |
| 2016/0272940 A1 | 9/2016 | Chung |
| 2017/0183627 A1 | 6/2017 | Fossati et al. |
| 2017/0239373 A1 | 8/2017 | Chen et al. |
| 2017/0292112 A1 | 10/2017 | Chang et al. |
| 2018/0298333 A1 | 10/2018 | Marton et al. |
| 2019/0062700 A1 | 2/2019 | Nicholas et al. |
| 2020/0087622 A1 | 3/2020 | Nair et al. |
| 2021/0040443 A1 | 2/2021 | Nicholas et al. |
| 2021/0047618 A1 | 2/2021 | Clevers et al. |
| 2022/0177835 A1 | 6/2022 | Studer et al. |
| 2022/0315891 A1 | 10/2022 | Amini |
| 2023/0027059 A1 | 1/2023 | Amini |
| 2023/0332103 A1 | 10/2023 | Amini et al. |
| 2024/0043798 A1 | 2/2024 | Amini |
| 2024/0117303 A1 | 4/2024 | Amini |
| 2024/0158743 A1 | 5/2024 | Amini |
| 2024/0158744 A1 | 5/2024 | Amini |

FOREIGN PATENT DOCUMENTS

| | | |
|---|---|---|
| CN | 110042082 A | 7/2019 |
| EP | 3031908 A1 | 6/2016 |
| WO | 2012/162124 A1 | 11/2012 |
| WO | 2013/163228 A1 | 10/2013 |
| WO | 2016/103269 A1 | 6/2016 |
| WO | 2016/162747 A2 | 10/2016 |
| WO | 2018/208836 A1 | 11/2018 |
| WO | 2020/219696 A1 | 10/2020 |
| WO | 2021/119209 A1 | 6/2021 |
| WO | 2021/224496 A1 | 11/2021 |
| WO | 2023003621 A1 | 1/2023 |
| WO | 2023/010897 A1 | 2/2023 |
| WO | 2023/075913 A1 | 5/2023 |

OTHER PUBLICATIONS

Zhang et al. Small Molecules Efficiently Reprogram Human Astroglial Cells into Functional Neurons. Cell Stem Cell 17: 735-747. (Year: 2015).*
Wen et al. Mesencephalic Astrocyte-Derived Neurotrophic Factor (MANF) Regulates Neurite Outgrowth Through the Activation of Akt/mTOR. Front. Mol. Neurosci. 13:1-17. (Year: 2020).*
De Angelis et al. Short-term retinoic acid treatment sustains pluripotency and suppresses differentiation of human induced pluripotent stem cells. Cell Death and Disease 9:1-13. (Year: 2018).*
Adams et al. Intrinsic and extrinsic regulators of oligodendrocyte progenitor proliferation and differentiation. Seminars in Cell and Developmental Biology 116: 16-24. 2021. Available Oct. 2020 (Year: 2021).*
Zhou et al. A Revolution in Reprogramming: Small Molecules. Current Molecular Medicine 19: 77-90. (Year: 2019).*
Zhang_Excel. Zhang et al. Supplemental Small Molecules Efficiently Reprogram Human Astroglial Cells into Functional Neurons. Cell Stem Cell 17: 48 pages. (Year: 2015).*
Med Chem Express (Akt). https://www.medchemexpress.com/Targets/Akt.html?effectName=Activator&page=3 (Year: 2024).*
Algarni et al. Activation of transglutaminase 2 by nerve growth factor in differentiating neuroblastoma cells: A role in cell survival and neurite outgrowth. European Journal of Pharmacology 820: 113-129. (Year: 2018).*
Tang et al. (Cell Phys Biochem 43:852-869. 2017) (Year: 2017).*
International Preliminary Report on Patentability, PCT/US2022/014306, dated Oct. 12, 2023, 10 pages.
Kriks, S. et al., Cleo: Applications and Technology 2019 San Jose, California United States May 5-10, 2019, vol. 480, No. 7378, Dec. 1, 2011 (Dec. 1, 2011), pp. 547-551, XP055771146, DOI: 10.1038/nature10648.

(Continued)

*Primary Examiner* — Arthur S Leonard
*Assistant Examiner* — Keenan A Bates
(74) *Attorney, Agent, or Firm* — Clark & Elbing LLP

(57) ABSTRACT

Methods for generating pre-oligodendrocyte progenitor cells (pre-OPCs) and oligodendrocyte progenitor cells (OPCs) from human pluripotent stem cells are provided using chemically-defined culture media that allow for generation of pre-OPCs and OPCs in as little as three days. Culture media, isolated cell populations and kits are also provided.

4 Claims, 12 Drawing Sheets

(56) References Cited

OTHER PUBLICATIONS

Playne R. et al., "Understanding Parkinson's Disease through the Use of Cell Reprogramming," Stem Cells Reviews and Reports, vol. 13(2):151-169 (2017).
Brodski C. et al., "Crosstalk of Intercellular Signaling Pathways in the Generation of Midbrain Dopaminergic Neurons In Vivo and from Stem Cells," Journal of Developmental Biology, vol. 7(1):p. 3 (2019).
International Search Report and Written Opinion, PCT/US2023/022819, dated Oct. 23, 2023, 13 pages.
Bukys, M. et al., "High-Dimensional Design-of-Experiments Extracts Small-Molecule-Only Induction Conditions for Dorsal Pancreatic Endoderm from Pluripotency," Iscience, vol. 23(8):101346: 35 pages (2020).
Douvaras & Fossati, "Generation and isolation of oligodendrocyte progenitor cells from human pluripotent stem cells," Nature Protocols, vol. 10(8):1143-1154 (2015).
Douvaras, P. et al., "Efficient generation of myelinating oligodendrocytes from primary progressive multiple sclerosis patients by induced pluripotent stem cells," Stem Cell Reports, vol. 3(2):250-259 (2014).
Garcia Leon, J-A. et al., "Generation of oligodendrocytes and establishment of an all-human myelinating platform from human pluripotent stem cells," Nature Protocols, vol. 15 (11):3716-3744 (2020).
Garcia-Leon, J. et al., "SOX10 Single Transcription Factor-Based Fast and Efficient Generation of Oligodendrocytes from Human Pluripotent Stem Cells," Stem Cell Reports, vol. 10(2):655-672 (2018).
Hu, B-Y. et al., "Differentiation of human oligodendrocytes from pluripotent stem cells," Nature Protocols, vol. 4 (11):1614-1622 (2009).
International Search Report and Written Opinion, PCT/US2022/014306, dated May 16, 2022, 18 pages.
Livesey, M. et al., "Maturation and electrophysiological properties of human pluripotent stem cell-derived oligodendrocytes," Stem Cells 34(4):1040-1053 (2016).
Namchaiw, P. et al., "Temporal and partial inhibition of GLI1 in neural stem cells (NSCs) results in the early maturation of NSC derived oligodendrocytes in vitro," Stem Cell Res & Therapy, vol. 10(1):272 (2019).
Piao, J. et al., "Human embryonic stem cell-derived oligodendrocyte progenitors remyelinate the brain and rescue behavioral deficits following radiation," Cell Stem Cell 16(2):198-210 (2015).
Thomson, J.A. et al. "Embryonic Stem Cell Lines Derived from Human Blastocysts," Science, vol. 282 (5391):1145-1147 (1998).
Tyler W. A.et al., "Activation of the Mammalian Target of Rapamycin (mTOR) Is Essential for Oligodendrocyte Differentiation," The Journal of Neuroscience, vol. 29(19):6367-6378 (2009).
Walaa F. Alsanie et al., "Human Embryonic Stem Cell-Derived Oligodendrocytes: Protocols and Perspectives," Stem Cells and Development, vol. 22(18):2459-2476 (2013).
Wang, S. et al., "Human iPSC-derived oligodendrocyte progenitor cells can myelinate and rescue a mouse model of congenital hypomyelination," Cell Stem Cell, vol. 12(2):252-264 (2013).
Yamashita, T. et al., "Differentiation of oligodendrocyte progenitor cells from dissociated monolayer and feeder-free cultured pluripotent stem cells," PLOS One, vol. 12(2): e0171947: 16 pages (2017).
Yu, J. et al. "Human induced pluripotent stem cells free of vector and transgene sequences," Science 324 (5928):797-801 (2009).
Arenas, E. et al., "How to make a midbrain dopaminergic neuron," Development, vol. 142(11):1918-1936 (2015).
Cooper, O. et al., "Differentiation of human ES and Parkinson's disease iPS cells into ventral midbrain dopaminergic neurons requires a high activity form of SHH, FGF8a and specific regionalization by retinoic acid," Mol. Cell. Neurosci, vol. 45:258-266 (2010).
Drummond, N. et al., "Cryopreservation of Human Midbrain Dopaminergic Neural Progenitor Cells Poised for Neuronal Differentiation," Front. Cell. Dev. Biol., vol. 8:578907 (2020).
Fedele, S. et al., "Expansion of human midbrain floor plate progenitors from induced pluripotent stem cells increases dopaminergic neuron differentiation potential," Sci. Reports, vol. 7:6036 (2017).
Ferri, A. et al., "Foxa1 and Foxa2 regulate multiple phases of midbrain dopaminergic neuron development in a dosage-dependent manner," Development, vol. 134:2761-2769 (2007).
Gantner, C. et al., "An Optimized Protocol for the Generation of Midbrain Dopamine Neurons under Defined Conditions," Star Protocols, vol. 1(2):100065 (2020).
Hartfield et al., "Physiological characterisation of human iPS-derived dopaminergic neurons," PLoS One, vol. 92: e87388 (2014).
International Search Report and Written Opinion, PCT/US2022/041663, dated Dec. 13, 2022, 23 pages.
International Search Report and Written Opinion, PCT/US2022/029979, dated Jan. 4, 2023, 17 pages.
Kim, S. et al., Neural stem cells derived from human midbrain organoids as a stable source for treating Parkinson's disease Midbrain organoid-NSCs (Og-NSC) as a stable source for PD treatment, Progress in Neurobiology, vol. 204 (2021).
Kriks, S. et al., "Floor plate-derived dopamine neurons from hESCs efficiently engraft in animal models of PD," Nature, vol. 480(7387):547-551 (2011).
Liu, Y. et al., "Directed differentiation of forebrain GABA interneurons from human pluripotent stem cells," Nature Protocols, vol. 8(9):1670-1679 (2013).
Maroof, A. et al., "Directed Differentiation and Functional Maturation of Cortical Interneurons from Human Embryonic Stem Cells," Cell Stem Cell, vol. 12(5):559-572 (2013).
Nicholas, C. et al., "Functional Maturation of hPSC-Derived Forebrain Interneurons Requires an Extended Timeline and Mimics Human Neural Development," Cell Stem Cell, vol. 12(5):573-586 (2013).
Nolbrant, S. et al., "Generation of high-purity human ventral midbrain dopaminergic progenitors for in vitro maturation and intracerebral transplantation," Nature Protocols, vol. 12(9):1962-1979 (2017).
Precious, S. et al., "Dopaminergic Progenitors Derived From Epiblast Stem Cells Function Similarly to Primary VM-Derived Progenitors When Transplanted Into a Parkinson's Disease Model," Front. Neurosci., vol. 14:312 (2020).
Qu Q. et al., "High-efficiency motor neuron differentiation from human pluripotent stem cells and the function of Islet-1," NAture Communications, vol. 5 (1): (2014).
Riemens, R. et al., "Directing neuronal cell fatein vitro: Achievements and challenges," Progress in Neurobiology, vol. 168: 42-68 (2018).
Urbanek, P. et al., Cooperation of Pax2 and Pax5 in midbrain and cerebellum development, Proc. Natl. Acad. Sci., vol. 94(11):5703-5708 (1997).
Vernay, B. et al. "Otx2 regulates subtype specification and neurogenesis in the midbrain," J. Neurosci., vol. 25 (19):4856-4867 (2005).
Wang, M. et al., "Development and Differentiation of Midbrain Dopaminergic Neuron: From Bench to Bedside ," Cells, vol. 9:1489 (2020).
Yan, C. et al., "Lmx1a and lmx1b function cooperatively to regulate proliferation, specification, and differentiation of midbrain dopaminergic progenitors," J. Neurosci., vol. 31(35):12413-12425 (2011).
Yang, H. et al., "Generation of functional dopaminergic neurons from human spermatogonial stem cells to rescue parkinsonian phenotypes," Stem Cell Res. Therap., vol. 10(1):195 (2019).
Alvarez-Dolado, M. et al., "Cortical inhibition modified by embryonic neural precursors grafted into the postnatal brain," J. Neurosci., vol. 26(28):7380-7389 (2006).
Baraban, S.et al., "Reduction of seizures by transplantation of cortical GABAergic interneuron precursors into Kv1.1 mutant mice," Proc. Natl. Acad. Sci., vol. 106(36):15472-15477 (2009).
Batista-Brito, R. et al., "The cell-intrinsic requirement of Sox6 for cortical interneuron development," Neuron, vol. 63:466-481 (2009).
Comella-Bolla, A. et al., "Human Pluripotent Stem Cell-Derived Neurons Are Functionally Mature In Vitro and Integrate into the Mouse Striatum Following Transplantation," Mol. Neurobiol. vol. 57(6):2766-2798 (2020).

(56) References Cited

OTHER PUBLICATIONS

Crompton, L. et al., "Stepwise, non-adherent differentiation of human pluripotent stem cells to generate basal forebrain cholinergic neurons via hedgehog signaling," Stem Cell Res., vol. 11:1206-1221 (2013).
Feigenson, K. et al., "Canonical Wnt signalling requires the BMP pathway to inhibit oligodendrocyte maturation," ASN Neuro, vol. 3 (3)(art:e00061):147-158 (2011) doi:10.1042/AN20110004.
Fishell and Rudy, "Mechanisms of inhibition within the telencephalon: "where the wild things are,"" Annu. Rev. Neurosci., vol. 34:535:567 (2011).
Goldman, S.A. et al., "How to make an oligodendrocyte," Development, vol. 142(23):3983-3995 (2015).
Guardiola-Diaz, H. et al., "Erk1/2 MAPK and mTOR Signaling Sequentially Regulates Progression Through Distinct Stages of Oligodendrocyte Differentiation," Glia., vol. 60(3): 476-486 (2012) doi:10.1002/glia.22281.
Guo, C. et al., "Fezf2 expression identifies a multipotent progenitor for neocortical projection neurons, astrocytes, and oligodendrocytes," Neuron, vol. 80(5):1167-1174. (2013).
Gusel'Nikova et al., "NeuN as a Neuronal Nuclear Antigen and Neuron Differentiation Marker," Acta Naturae, vol. 7:42-47 (2015).
Hansen et al., "Non-epithelial stem cells and cortical interneuron production in the human ganglionic eminences (MGE)," Nature Neurosci., vol. 16(11):1576-1587 (2013).
Hoch, R. et al., "OTX2 Transcription Factor Controls Regional Patterning within the Medial Ganglionic Eminence and Regional Identity of the Septum," Cell Reports, vol. 12(3):482-494 (2015).
Horn and Nicoll, "Somatostatin and parvalbumin inhibitory synapses onto hippocampal pyramidal neurons are regulated by distinct mechanisms," Proc. Natl. Acad. Sci., vol. 115(3):589-594 (2018).
Huebner, L. et al., "FEZF2's Role in Differentiation and Proliferation in Radial Glial Cells During Cortical Development," University of California, Santa Cruz Dissertations Publishing, pp. 1-33 (2020).
Ihnatovych, I. et al., "Timing of Wnt Inhibition Modulates Directed Differentiation of Medial Ganglionic Eminence Progenitors from Human Pluripotent Stem Cells," Stem Cells International, vol. 2018, Article ID 3983090, 11 pages (2018).
International Preliminary Report on Patentability, PCT/US2022/029979, dated Jan. 18, 2024, 7 pages.
International Preliminary Report on Patentability, PCT/US2022/041663, dated Apr. 30, 2024, 14 pages.
International Search Report and Written Opinion, PCT/US2023/024792, dated May 22, 2024, 11 pages.
Jang, Y. et al., "Retinoic acid-mediated induction of neurons and glial cells from human umbilical cord-derived hematopoietic stem cells," Journal of Neuroscience Research, vol. 75(4): 573-584 (2004).
Yashar, M. et al, "Wnt-mediated self-renewal of neural stem/progenitor cells," PNAS, vol. 105(44):16970-16975 (2008).
Kioussi, C. et al., "Pax6 is essential for establishing ventral-dorsal cell boundaries in pituitary gland development," Proc. Natl. Acad. Sci., vol. 96(25):14378-14382 (1999).
Lagutin et al., "Six3 repression of Wnt signaling in the anterior neuroectoderm is essential for vertebrate forebrain development," Genes & Development, vol. 17(3):368-379 (2003).
Le Magueresse and Monyer, "GABAergic interneurons shape the functional maturation of the cortex," Neuron 77(3):388-405 (2013).
Leoni, G. et al., "NG2 cells differentiate into astrocytes in cerebellar slices," Molecular and Cellular Neuroscience, vol. 42(3): 208-218 (2009).
Liu, Y. et al., "Oligodendrocyte and Astrocyte Development in Rodents: An In Situ and Immunohistological Analysis During Embryonic Development," Glia, vol. 40(1): 25-43 (2002).
Lybrand, Z. et al., "Stem cells: A path towards improved epilepsy therapies," Neuropharm., vol. 168:107781 (2020).
Marques, S. et al., "Transcriptional Convergence of Oligodendrocyte Lineage Progenitors during Development," Developmental Cell, vol. 46(4): 504-517 (2018).
Mayer, C. et al., "Developmental diversification of cortical inhibitory interneurons," Nature, 555(7697):457-462 (2018).
McCaughey-Chapman, A. et al., "Cell reprogramming for oligodendrocytes: A review of protocols and their applications to disease modeling and cell-based remyelination therapies," Journal of Neuroscience Research, vol. 101(6):1000-1028 (2023).
Nahar, L. et al., "The Role of Parvalbumin Interneurons in Neurotransmitter Balance and Neurological Disease," Front. Psych., vol. 12:679960 (2021).
Nguyen, R. et al., "Parvalbumin and GAD65 interneuron inhibition in the ventral hippocampus induces distinct behavioral deficits relevant to schizophrenia," J. Neurosci., vol. 34(45):14948-14960 (2014).
Pai, E. et al., "Maf and Mafb control mouse pallial interneuron fate and maturation through neuropsychiatric disease gene regulation," Elife, vol. 9:54903 (2020).
Shetty and Upadhya, "GABA-ergic cell therapy for epilepsy: Advances, limitations and challenges," Neurosci. Biobehav. Rev., vol. 62:35-47 (2016).
Shi, Z. et al., "Conversion of Fibroblasts to Parvalbumin Neurons by One Transcription Factor, Ascl1, and the Chemical Compound Forskolin," J. Biol. Chem., vol. 291(26):13560-13570 (2016).
Silberberg, S. et al., "Subpallial Enhancer Transgenic Lines: a Data and Tool Resource to Study Transcriptional Regulation of GABAergic Cell Fate," Neuron, vol. 92(1):59-74 (2016).
Stoykova, A. et al., "Pax6 modulates the dorsoventral patterning of the mammalian telencephalon," J. Neurosci. 20(21):8042-8050 (2000).
Trotter, J. et al., "NG2 cells: Properties, progeny and origin," Brain Research Reviews, vol. 63(1-2): 72-82 (2010).
Wang, Y. et al., "Dlx5 and Dlx6 regulate the development of parvalbumin-expressing cortical interneurons," J. Neurosci., vol. 30(15):5334-5345 (2010).
Yan, Y. et al., "Efficient and rapid derivation of primitive neural stem cells and generation of brain subtype neurons from human pluripotent stem cells," Stem Cells Transl. Med., vol. 2(11):862-870 (2013).
Yuan, F. et al, "Efficient generation of region-specific forebrain neurons from human pluripotent stem cells under highly defined condition," Sci Rep., vol. 5:18550 (2015).
Yuan, F. et al., "Induction of human somatostatin and parvalbumin neurons by expressing a single transcription factor LIM homeobox 6," Elife, vol. 7:e37382 (2018).
Zhang, S. et al., "Fezf2 promotes neuronal differentiation through localised activation of Wnt/ß-catenin signalling during forebrain development," Development, vol. 141(24):4794-47805 (2014).

\* cited by examiner

| | Response | Criterion | Value | Graph | log(D) | Prob. of failure | Cpk |
|---|---|---|---|---|---|---|---|
| 24 | MAFB | Predicted | 262.762 | | | | |
| 25 | MAF | Predicted | 1513.6 | | | | |
| 26 | MEF2C | Predicted | 32.2549 | | | | |
| 27 | MKI67 | Predicted | 4271.5 | | | | |
| 28 | NETO1 | Predicted | 84.0921 | | | | |
| 29 | NETO2 | Predicted | 5207.9 | | | | |
| 30 | NEUROD6 | Predicted | 61.0956 | | | | |
| 31 | NKX2-1 | Predicted | 3594.47 | | | | |
| 32 | NKX2-2 | Maximize | 12480.6 | | -1.34983 | 19% | 0.29305 |
| 33 | NPAS1 | Predicted | 6.28653 | | | | |
| 34 | NPY | Predicted | 24.7324 | | | | |
| 35 | NR2F1 | Predicted | 3138.48 | | | | |
| 36 | NR2F2 | Predicted | 2196.53 | | | | |
| 37 | NKXPH1 | Predicted | -27.3136 | | | | |
| 38 | OLIG1 | Predicted | 129.939 | | | | |
| 39 | OLIG2 | Predicted | 1049.37 | | | | |
| 40 | PAX6 | Predicted | 1248.23 | | | | |
| 41 | PDGFRA | Predicted | 346.458 | | | | |
| 42 | POU3F2 | Predicted | 402.112 | | | | |
| 43 | PROX1 | Predicted | 613.532 | | | | |
| 44 | PVALB | Predicted | 158.934 | | | | |
| 45 | RELN | Predicted | 1271.24 | | | | |
| 46 | RUNX1T1 | Predicted | 261.165 | | | | |
| 47 | SATB1 | Predicted | 3604.89 | | | | |
| 48 | SOX10 | Predicted | -6.22496 | | | | |
| 49 | SOX2 | Predicted | 67561.9 | | | | |
| 50 | SP8 | Predicted | 254.048 | | | | |
| 51 | SST | Predicted | 3239.19 | | | | |
| 52 | TUBB3 | Predicted | 19466.2 | | | | |
| 53 | VIM | Predicted | 72202.5 | | | | |
| 54 | ZIC1 | Predicted | 1526.61 | | | | |

| | Factor | Role | Value | Graph | Factor contribution |
|---|---|---|---|---|---|
| 1 | PD0325901 | Free | 0.11493 | | 17.3982 |
| 2 | ZM336372 | Free | 0.000339067 | | 16.8484 |
| 3 | MK2206 | Free | 1.2371 | | 8.96926 |
| 4 | SC79 | Free | 0.999546 | | 1.47518 |
| 5 | AGN193109 | Free | 0.000804311 | | 1.7969 |
| 6 | TTNBP | Free | 49.9982 | | 31.2673 |
| 7 | AZD3147 | Free | 8.51318e-05 | | 8.46043 |
| 8 | MHY1485 | Free | 1.99996 | | 13.7844 |

FIG. 1

| | Response | Criterion | Value | Graph | log(D) | Prob. of failure | Cpk |
|---|---|---|---|---|---|---|---|
| 24 | MAFB | Predicted | 502.928 | | | | |
| 25 | MAF | Predicted | 1041.46 | | | | |
| 26 | MEF2C | Predicted | 292.265 | | | | |
| 27 | MKI67 | Predicted | 6304.16 | | | | |
| 28 | NETO1 | Predicted | 177.072 | | | | |
| 29 | NETO2 | Predicted | 4452.29 | | | | |
| 30 | NEUROD6 | Predicted | 122.783 | | | | |
| 31 | NKX2-1 | Predicted | 2232.01 | | | | |
| 32 | NKX2-2 | Predicted | 3335.38 | | | | |
| 33 | NPAS1 | Predicted | 1.41842 | | | | |
| 34 | NPY | Predicted | 38.0745 | | | | |
| 35 | NR2F1 | Predicted | 4260.34 | | | | |
| 36 | NR2F2 | Predicted | 4398.83 | | | | |
| 37 | NKXPH1 | Predicted | -5.47688 | | | | |
| 38 | OLIG1 | Predicted | 228.358 | | | | |
| 39 | OLIG2 | Predicted | 241.971 | | | | |
| 40 | PAX6 | Predicted | 7874.96 | | | | |
| 41 | PDGFRA | Maximize | 832.98 | | -0.60206 | 22% | 0.247347 |
| 42 | POU3F2 | Predicted | 239.865 | | | | |
| 43 | PROX1 | Predicted | 777.062 | | | | |
| 44 | PVALB | Predicted | 63.8672 | | | | |
| 45 | RELN | Predicted | 920.133 | | | | |
| 46 | RUNX1T1 | Predicted | 565.708 | | | | |
| 47 | SATB1 | Predicted | 3654.04 | | | | |
| 48 | SOX10 | Predicted | -4.01141 | | | | |
| 49 | SOX2 | Predicted | 56097.1 | | | | |
| 50 | SP8 | Predicted | 434.992 | | | | |
| 51 | SST | Predicted | 1861.62 | | | | |
| 52 | TUBB3 | Predicted | 13831 | | | | |
| 53 | VIM | Predicted | 26669.6 | | | | |
| 54 | ZIC1 | Predicted | 404.143 | | | | |

| | Factor | Role | Value | Graph | Factor contribution |
|---|---|---|---|---|---|
| 1 | PD0325901 | Free | 100 | | 30.0553 |
| 2 | ZM336372 | Free | 1 | | 0.427593 |
| 3 | MK2206 | Free | 0 | | 1.1434 |
| 4 | SC79 | Free | 0 | | 0.835633 |
| 5 | AGN193109 | Free | 0 | | 2.5985 |
| 6 | TTNBP | Free | 50 | | 49.0142 |
| 7 | AZD3147 | Free | 0 | | 2.46744 |
| 8 | MHY1485 | Free | 2 | | 13.4579 |

FIG. 2

| Objective | Setpoint (#19) | Alternative setpoints | | | | |
|---|---|---|---|---|---|---|
| Response | Criterion | Value | Graph | log(D) | Prob. of failure | Cpk |
| 19 HES1 | Predicted | 330.554 | | | | |
| 20 HMGB2 | Predicted | 14870.5 | | | | |
| 21 HMX2 | Predicted | -6.64705 | | | | |
| 22 HOXB1 | Predicted | -0.378681 | | | | |
| 23 IRX3 | Predicted | 696.214 | | | | |
| 24 ISL1 | Predicted | -26.1116 | | | | |
| 25 ISL2 | Predicted | -17.4699 | | | | |
| 26 LHX4 | Predicted | 68.0646 | | | | |
| 27 LMO1 | Predicted | 905.208 | | | | |
| 28 LMO3 | Predicted | 305.228 | | | | |
| 29 LMX1A | Predicted | 604.987 | | | | |
| 30 LMX1B | Predicted | -112.196 | | | | |
| 31 MKI67 | Predicted | 1461.79 | | | | |
| 32 NEUROD1 | Predicted | 0.550277 | | | | |
| 33 NEUDOD6 | Predicted | 22.9791 | | | | |
| 34 NEUROG1 | Predicted | 48.9105 | | | | |
| 35 NEUROG2 | Predicted | 57.2419 | | | | |
| 36 NFE2L3 | Predicted | 202.664 | | | | |
| 37 NKX6-2 | Predicted | 33.9382 | | | | |
| 38 NR2F6 | Predicted | 2901.11 | | | | |
| 39 NR4A2 | Predicted | 2.57416 | | | | |
| 40 OLIG2 | Predicted | 39.718 | | | | |
| 41 OTX2 | Maximize | 12755.9 | | -10 | 0.88% | 0.777651 |
| 42 PITX2 | Predicted | -5.0266 | | | | |
| 43 PITX3 | Predicted | 5.75851 | | | | |
| 44 POU4F1 | Predicted | 14.1262 | | | | |
| 45 SIX3 | Predicted | -2385.95 | | | | |
| 46 TCF3 | Predicted | 7666.44 | | | | |
| 47 TERF2 | Predicted | 1103.74 | | | | |
| 48 TH | Predicted | -0.189617 | | | | |
| 49 VIM | Predicted | 10365.4 | | | | |
| 50 WNT1 | Predicted | 447.584 | | | | |
| 51 WNT8B | Predicted | 157.511 | | | | |
| 52 LHX3 | Predicted | -0.494643 | | | | |

| | Factor | Role | Value | Graph | Factor contribution |
|---|---|---|---|---|---|
| 1 | LDN193189 | Free | 248.736 | | 11.9807 |
| 2 | PD173074+BLU9931 | Free | 49.994 | | 1.79948 |
| 3 | Purmorphamine 500 | Free | 18.6918 | | 2.03588 |
| 4 | Purmorphamine 200 | Free | 9.2549 | | 0.38661 |
| 5 | SC79 | Free | 0.988981 | | 5.75937 |
| 6 | MK2206 | Free | 124.722 | | 22.2839 |
| 7 | ZM336372 | Free | 0.415081 | | 3.84831 |
| 8 | PD0325901 | Free | 99.9991 | | 18.0824 |
| 9 | CHIR99021 | Free | 0.99711 | | 13.5337 |
| 10 | XAV939 | Free | 0.134963 | | 1.98982 |
| 11 | UCLA_GP130_2 | Free | 0.0207014 | | 3.64899 |
| 12 | Tofacitinib | Free | 0.2591 | | 12.0135 |
| 13 | GO6983 | Free | 95.5821 | | 2.63741 |

FIG. 4

| Objective | Setpoint (#8) | Alternative setpoints | | | | |
|---|---|---|---|---|---|---|
| Response | Criterion | Value | Graph | log(D) | Prob. of failure | Cpk |
| 1 RNA | Predicted | 240.061 | | | | |
| 2 ALDH1A1 | Predicted | 0.50181 | | | | |
| 3 ASCL1 | Predicted | 1.73552 | | | | |
| 4 BARHL1 | Predicted | 339.575 | | | | |
| 5 DBX2 | Predicted | 0.750382 | | | | |
| 6 DDC | Predicted | -0.676181 | | | | |
| 7 DMBX1 | Predicted | 613.121 | | | | |
| 8 EN1 | Predicted | 0.439595 | | | | |
| 9 EN2 | Predicted | -0.0220256 | | | | |
| 10 ETV4 | Predicted | 50.9694 | | | | |
| 11 FERD3L | Predicted | 51.6771 | | | | |
| 12 FEV | Predicted | -0.0817658 | | | | |
| 13 FEZF2 | Maximize | 4466 | | -10 | 0.02% | 1.25582 |
| 14 FOXA1 | Predicted | 142.511 | | | | |
| 15 FOXA2 | Predicted | 1111.45 | | | | |
| 16 FOXD2 | Predicted | 24.5731 | | | | |
| 17 GATA3 | Predicted | 253.497 | | | | |
| 18 GBX2 | Predicted | 1.25974 | | | | |
| 19 HES1 | Predicted | 996.596 | | | | |
| 20 HMGB2 | Predicted | 17929.3 | | | | |
| 21 HMX2 | Predicted | 19.6778 | | | | |
| 22 HOXB1 | Predicted | 0.384939 | | | | |
| 23 IRX3 | Predicted | 181.478 | | | | |
| 24 ISL1 | Predicted | 26.9557 | | | | |
| 25 ISL2 | Predicted | 118.897 | | | | |
| 26 LHX4 | Predicted | 541.817 | | | | |
| 27 LMO1 | Predicted | 1135.94 | | | | |
| 28 LMO3 | Predicted | 138.926 | | | | |
| 29 LMX1A | Predicted | 240.188 | | | | |
| 30 LMX1B | Predicted | 5.61555 | | | | |
| 31 MKI67 | Predicted | 2490.26 | | | | |
| 32 NEUROD1 | Predicted | 1.62807 | | | | |
| 33 NEUROD6 | Predicted | 44.8253 | | | | |
| 34 NEUROG1 | Predicted | 57.8583 | | | | |

| Factor | Role | Value | Graph | Factor contribution |
|---|---|---|---|---|
| 1 LDN193189 | Free | 244.52 | | 19.4571 |
| 2 PD173074+BLU9931 | Free | 38.0259 | | 5.11884 |
| 3 Purmorphamine 500 | Free | 488.02 | | 9.76177 |
| 4 Purmorphamine 200 | Free | 47.0196 | | 3.29792 |
| 5 SC79 | Free | 0.999847 | | 6.31136 |
| 6 MK2206 | Free | 124.995 | | 12.2943 |
| 7 ZM336372 | Free | 0.0372426 | | 9.80767 |
| 8 PD0325901 | Free | 98.3146 | | 14.5858 |
| 9 CHIR99021 | Free | 0.809146 | | 5.31386 |
| 10 XAV939 | Free | 99.9993 | | 12.5423 |
| 11 UCLA_GP130_2 | Free | 0.564196 | | 0.385926 |
| 12 Tofacitinib | Free | 72.4413 | | 0 |
| 13 GO6983 | Free | 34.9768 | | 1.12322 |

FIG. 5

METHODS AND COMPOSITIONS FOR GENERATING OLIGODENDROCYTE PROGENITOR CELLS

RELATED APPLICATIONS

This application claims priority to U.S. Provisional Application No. 63/168,065, filed Mar. 30, 2021, the entire contents of which is hereby incorporated by reference.

GOVERNMENT LICENSED RIGHTS

This invention was made with government support under Grant Number: W911NF-17-3-0003 awarded by the U.S. ARMY ACC-AGP-RTP. The government has certain rights in the invention.

BACKGROUND OF THE INVENTION

Oligodendrocytes (OLs) are a type of glial cells that synthesize the myelin sheath around axons. Thus, they are critical for nerve conduction in the central nervous system (CNS). A greater understanding of oligodendrocyte biology is likely to be very important in the development of therapies for the treatment of neurodegenerative disorders, including demyelinating diseases, such as multiple sclerosis and leukodystrophies, as well as amyotrophic lateral sclerosis (ALS), which can involve demyelination later in the course of the disease. Additionally, radiation therapy to the brain can be associated with the side-effect of oligodendrocyte depletion, leading to cognitive decline and/or impairment of motor coordination.

Since mature human oligodendrocytes are not readily isolatable from human subjects, human oligodendrocyte cell lines have been developed to allow study of the cells. However, immortalized cell lines may not mimic the full biology of the native cells and are not suitable for therapeutic uses. Thus, the ability to generate human oligodendrocytes in vitro, such as from stem cells, is highly desirable. Various protocols have been reported for differentiation of oligodendrocytes from human pluripotent stem cells. However, these protocols remain inefficient and variable in terms of oligodendrocyte yield and require very long differentiation times to generate myelin basic protein (MBP)-positive oligodendrocytes.

An early protocol used a four-step process (Hu et al. (2009) *Nature Protocols* 4:1614-1622; see also Wang et al. (2013) *Cell Stem Cell* 12:252-264). The protocol first involved induction of human embryonic stem cells (hESCs) to differentiate into neuroepithelial cells for two weeks, forming neural-tube like rosettes, followed by a 10 day treatment with retinoic acid (RA) and sonic hedgehog (SHH), leading to OLIG2-expressing progenitors. Treatment with fibroblast growth factor (FGF2) for another 10 days led to conversion to OLIG2 and NKX2.2-expressing pre-OPCs. Finally, the pre-OPCs were cultured for an additional 8-9 weeks in the absence of FGF2 to differentiate into OPCs, expressing markers such as platelet-derived growth factor receptor alpha (PDGFRα), SOX10 and NG2. Thus, using this protocol, it required approximately 24 days to generate OLIG2-expressing progenitors and approximately 34 days to generate OLIG2 and NKX2.2-expressing pre-OPCs, with about 100 days needed to obtain mature Ols. A variant of this protocol was reported by Douvaras et al. (*Stem Cell Reports* (2014) 3:250-259), but still required about 20 days to obtain pre-OPCs and about 50 days to obtain OPCs, including culture with exogenously-added growth factors PDGF, IGF-1 and HGF.

Subsequently, alternative protocols have been reported, yet these protocols still utilized an approximately week-long neural induction and patterning phase (also referred to as neuralization), followed by induction of cells expressing pre-OPC and OPC markers using media that included exogenously-added growth factors, such as FGF2, PDGF, IGF-1 and/or HGF depending on the protocol (see e.g., Piao et al. (2015) *Cell Stem Cell* 16:198-210; Douvaras & Fossati (2015) *Nature Protocols* 10:1143-1154; Livesey et al. (2016) *Stem Cells* 34:1040-1053; and Yamashita et al. (2017) *PLOS One* 12: e0171947).

More recently, a protocol has been reported in which hESCs were first neurally induced to generate neural progenitor cells (NPCs), followed by overexpression of the SOX10 transcription factor in the NPCs (via viral transduction) and expansion in the presence of bFGF, leading to generation of MBP-positive oligodendrocytes in only about 20 days (Garcia-Leon et al. (2018) *Stem Cell Reports* 10:655-672). Furthermore, transient and partial inhibition of the SHH pathway transcription factor GLI1 in neural stem cells (generated by neuralization) by a small molecule inhibitor GANT61 was found to generate OPCs that were more migratory and could differentiate earlier toward myelin-producing oligodendrocytes (Namchaiw et al. (2019) *Stem Cell Res & Therapy* 10:272).

Accordingly, while some progress has been, there remains a need for efficient and robust methods and compositions for generating oligodendrocyte progenitor cells from human pluripotent stem cells.

SUMMARY OF THE INVENTION

This disclosure provides methods of generating human pre-OPCs and OPCs from pluripotent stem cells using chemically-defined culture media that allows for generation of OLIG2 and NKX2.2-positive pre-OPCs and OPCs in as little as three days of culture. The culture media lacks serum or other exogenously-added growth factors and comprises small molecule agents that either agonize or antagonize particular signaling pathway activity in the pluripotent stem cells such that differentiation along the OPC lineage is promoted, leading to cellular maturation and expression of OPC-associated biomarkers. The methods of the disclosure have the advantage that they bypass the neural induction step of prior art protocols and allow for direct differentiation of pluripotent stem cells to pre-OPCs and OPCs, thereby significantly shortening the time needed to generate pre-OPCs and OPCs. Moreover, the use of small molecule agents in the culture media allows for precise control of the culture components.

Accordingly, in one aspect, the disclosure pertains to a method of generating human pre-oligodendrocyte progenitor cells (pre-OPCs) or oligodendrocyte progenitor cells (OPCs) comprising:

culturing human pluripotent stem cells in a culture media lacking exogenously-added growth factors and comprising a retinoic acid (RA) pathway agonist, an Akt pathway agonist and an mTOR pathway agonist, such that OLIG2-expressing pre-OPCs or OPCs are generated.

In one embodiment, the OLIG2-expressing pre-OPCs or OPCs are generated within 72 hours of starting culture of the human pluripotent stem cells in the culture media. In one embodiment, the pre-OPCs or OPCs also express NKX2-2.

In another embodiment, the culture media further comprises a WNT pathway antagonist. In another embodiment, the culture media further comprises an SHH pathway agonist. In another embodiment, the culture media further comprises a BMP pathway antagonist. In another embodiment, the culture media further comprises a PKC pathway antagonist. In various embodiments, the pre-OPCs or OPCs also express OTX2 and/or FEZF2.

Accordingly, in another aspect, the disclosure pertains to a method of generating human pre-oligodendrocyte progenitor cells (pre-OPCs) or oligodendrocyte progenitor cells (OPCs) comprising:
culturing human pluripotent stem cells in a culture media lacking exogenously-added growth factors and comprising a retinoic acid (RA) pathway agonist, an Akt pathway agonist, an mTOR pathway agonist, a WNT pathway antagonist, an SHH pathway agonist, a BMP pathway antagonist and a PKC pathway antagonist such that OLIG2-expressing pre-OPCs or OPCs are generated. In other embodiments, the pre-OPCs or OPCs also express NKX2-2, OTX2 and/or FEZF2.

Non-limiting examples of suitable agonist and antagonist agents, and concentrations therefor, are described in further detail herein.

In one embodiment, the human pluripotent stem cells are induced pluripotent stem cells (iPSCs). In another embodiment, the human pluripotent stem cells are embryonic stem cells.

In on embodiment, the human pluripotent stem cells are attached to vitronectin-coated plates during culturing.

In another aspect, the disclosure pertains to a culture media for obtaining pre-oligodendrocyte progenitor cells (pre-OPCs) or oligodendrocyte progenitor cells (OPCs) comprising a retinoic acid (RA) pathway agonist, an Akt pathway agonist and an mTOR pathway agonist and lacking exogenously-added growth factors. In one embodiment, the culture media further comprises a WNT pathway antagonist In one embodiment, the culture media further comprises an SHH pathway agonist. In one embodiment, the culture media further comprises a BMP pathway antagonist. In one embodiment, the culture media further comprises a PKC pathway antagonist.

In another aspect, the disclosure pertains to an isolated cell culture of pre-oligodendrocyte progenitor cells (pre-OPCs) or oligodendrocyte progenitor cells (OPCs), the culture comprising: OLIG2-expressing pre-OPCs or OPCs cultured in a culture media comprising a retinoic acid (RA) pathway agonist, an Akt pathway agonist and an mTOR pathway agonist and lacking exogenously-added growth factors. In one embodiment, the culture media further comprises a WNT pathway antagonist In one embodiment, the culture media further comprises an SHH pathway agonist. In one embodiment, the culture media further comprises a BMP pathway antagonist. In one embodiment, the culture media further comprises a PKC pathway antagonist. In other embodiments, the pre-OPCs or OPCs also express NKX2-2, OTX2 and/or FEZF2. In one embodiment of the cell culture, the pre-OPCs or OPCs are attached to vitronectin-coated plates.

In another aspect, the disclosure pertains to a pre-oligodendrocyte progenitor cells (pre-OPCs) or oligodendrocyte progenitor cell (OPC), such as generated by a method of the disclosure. In one embodiment, the disclosure provides a composition comprising a non-native pre-oligodendrocyte progenitor cells (pre-OPCs) or oligodendrocyte progenitor cell (OPC), wherein the pre-OPC or OPC expresses OLIG2, NKX2-2, OTX2 and FEZF2 and lacks expression of NESTIN.

In yet another aspect, the disclosure pertains to an isolated cell population of pre-oligodendrocyte progenitor cells (pre-OPCs) or oligodendrocyte progenitor cells (OPCs) comprising at least $1\times10^6$ OLIG2-expressing pre-OPCs or OPCs, wherein the cell population lacks NESTIN-expressing neural stem cells. In other embodiments, the pre-OPCs or OPCs also express NKX2-2, OTX2 and/or FEZF2. In one embodiment of the isolated cell population, the pre-OPCs or OPCs are bound with at least one antibody that binds at least one cell surface marker expressed by the pre-OPCs or OPCs.

In yet another aspect, the disclosure pertains to a method of isolating pre-oligodendrocyte progenitor cells (pre-OPCs) or oligodendrocyte progenitor cells (OPCs), the method comprising:
contacting the OLIG2-expressing pre-OPCs or OPCs generated by a method of the disclosure, with at least one binding agent that binds to a cell surface marker expressed by the OLIG2-expressing pre-OPCs or OPCs; and
isolating cells that bind to the binding agent to thereby isolate OPCs.

In one embodiment, the binding agent is an antibody.

Other features and advantages of the invention will be apparent from the following detailed description and claims.

BRIEF DESCRIPTION OF THE DRAWINGS

FIG. 1 shows results from an HD-DoE model of an 8-factor experiment optimized for maximum expression of NKX2-2. The upper section of the model shows the prediction of expression level of pre-selected 53 genes when optimized for NKX2-2. The lower section of the model shows the effectors that were tested in this model and their contribution to maximum expression of NKX2-2. The value column refers to required concentration of each effector to mimic the model.

FIG. 2 shows the results from an HD-DoE model of an 8-factor experiment optimized for maximum expression of PDGFRA. Upper and lower sections are as described for FIG. 1. This condition highlights the effector PD0325901 with factor contribution of 30.05 as an important input for high expression of PDGFRA.

FIG. 4 shows the results from an HD-DoE model of a 13-factor experiment optimized for maximum expression of OTX2. This model introduced MK2206, PD0325901, CHIR99021, LDN193189, Go6983 and PD173074 as positive effectors on expression of OTX2.

FIG. 5 shows the results from an HD-DoE model of a 13-factor experiment optimized for maximum expression of FEZF2. This model confirmed the positive effect of LDN193189, MK2206 and PD0325901 on patterning the cells and introduced three other factors including SC79, XAV939 and Purmorphamine-500 nM.

DETAILED DESCRIPTION OF THE INVENTION

Figure 3:
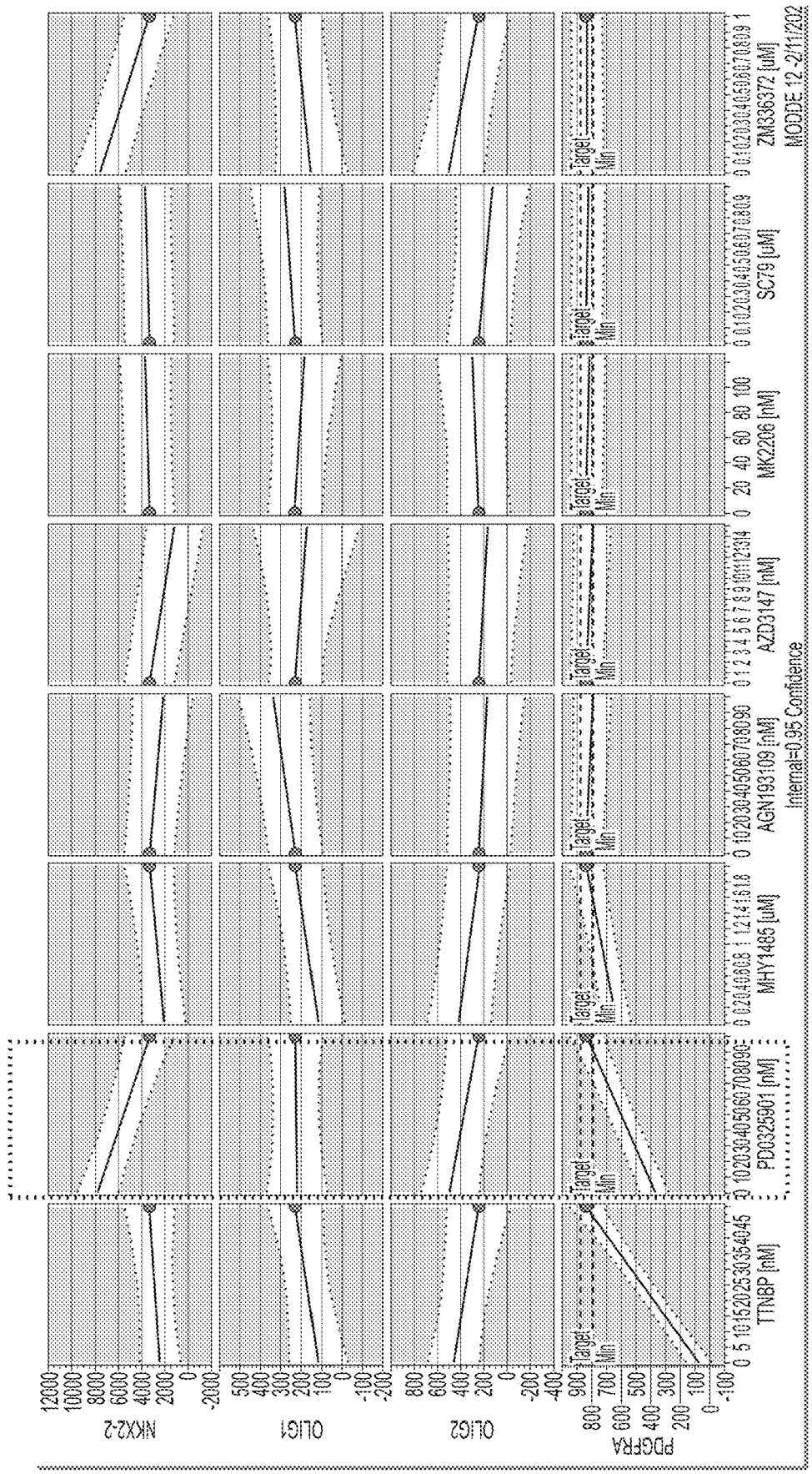
FIG. 3 shows the dynamic profile of expression levels of NKX2-2, OLIG1, OLIG2 and PDGFRA genes relative to the concentration of 8 effectors tested. The positive impact of TTNPB, MHY1485 and PD0325901 on expression of PDG-FRA and their factor contribution is shown by the slope of the plots for each effector. The dotted box highlights the opposite impact of PD0325901 on NKX2-2 and OLIG2 compared to PDGFRA.

Described herein are methodologies and compositions that allow for the generation of pre-OPCs and OPCs from human pluripotent stem cells under chemically-defined culture conditions using a small molecule based approach. The methods of the disclosure have the advantage that the starting pluripotent stem cells do not go through neural induction, which many prior art protocols use. This allows for generation of pre-OPCs and OPCs in as little as three days, which is significantly shorter than current protocols, which average 10 days to generate pre-OPCs.

As described in Example 1, a High-Dimensional Design of Experiments (HD-DoE) approach was used to simultaneously test multiple process inputs (e.g., small molecule agonists or antagonists) on output responses, such as gene expression. These experiments allowed for the identification of chemically-defined culture media, comprising agonists and/or antagonists of particular signaling pathways, that is sufficient to generate pre-OPCs or OPCs in a very short amount of time. The optimized culture media was further validated by a factor criticality analysis, which examined the effects of eliminating individual agonist or antagonist agents, as described in Example 2. Immunohistochemistry further confirmed the phenotype of the cells generated by the differentiation protocol, as described in Example 3.

Various aspects of the invention are described in further detail in the following subsections.

I. Cells

The starting cells used in the cultures of the disclosure are human pluripotent stem cells. As used herein, the term "human pluripotent stem cell" (abbreviated as hPSC) refers to a human stem cell that has the capacity to differentiate into a variety of different cell types. The term "pluripotent" as used herein refers to a cell with the capacity, under different conditions, to differentiate to cell types characteristic of all three germ cell layers (endoderm, mesoderm and ectoderm). Pluripotent cells are characterized primarily by their ability to differentiate to all three germ layers, for example, using a nude mouse and teratomas formation assay. Pluripotency can also evidenced by the expression of embryonic stem (ES) cell markers, although the preferred test for pluripotency is the demonstration of the capacity to differentiate into cells of each of the three germ layers.

Human pluripotent stem cells include, for example, induced pluripotent stem cells (iPSC) and human embryonic stem cells, such as ES cell lines. Non-limiting examples of induced pluripotent stem cells (iPSC) include 19-11-1, 19-9-7 or 6-9-9 cells (e.g, as described in Yu, J. et al. (2009) *Science* 324:797-801). Non-limiting examples of human embryonic stem cell lines include ES03 cells (WiCell Research Institute) and H9 cells (Thomson, J. A. et al. (1998) *Science* 282:1145-1147). Human pluripotent stem cells (PSCs) express cellular markers that can be used to identify cells as being PSCs. Non-limiting examples of pluripotent stem cell markers include TRA-1-60, TRA-1-81, TRA-2-54, SSEA1, SSEA3, SSEA4, CD9, CD24, OCT3, OCT4, NANOG and/or SOX2. Since the methods of generating pre-OPCs and/or OPCs of the disclosure are used to differentiate (maturate) the starting pluripotent stem cell population, in various embodiments the pre-OPC and/or OPC cell populations generated by the methods of the disclosure lack expression of one or more stem cell markers selected from the group consisting of TRA-1-60, TRA-1-81, TRA-2-54, SSEA1, SSEA3, SSEA4, CD9, CD24, OCT3, OCT4, NANOG and/or SOX2

The pluripotent stem cells are subjected to culture conditions, as described herein, that induce cellular differentiation. As used herein, the term "differentiation" refers to the development of a cell from a more primitive stage towards a more mature (i.e. less primitive) cell, typically exhibiting phenotypic features of commitment to a particular cellular lineage. An early progenitor cell that can be derived from human PSCs by neural induction (neuralization) is a neural precursor cell (NPC). As used herein, a "neural precursor cell" or "NPC" refers to a stem cell-derived progenitor cell that expresses the type VI intermediate filament protein Nestin. Since the methods of generating pre-OPCs and/or OPCs of the disclosure avoid the use of neural induction, and thus do not generate NPCs, in various embodiments the cell populations generated by the methods of the disclosure lack Nestin-positive cells.

In one embodiment, the cells generated by the methods of the disclosure are pre-oligodendrocyte progenitor cells (pre-OPCs). As used herein, a "pre-oligodendrocyte progenitor cells" or "pre-OPC" refers to a stem cell-derived progenitor cell that expresses the cellular markers OLIG2 and NKX2.2. A pre-OPC may express additional markers, including but not limited to: OTX2 (anterior neuroectoderm biomarker), FEZF2 (anterior ectoderm biomarker), and/or OLIG1.

In one embodiment, the cells generated by the methods of the disclosure are oligodendrocyte progenitor cells (OPCs), which are more differentiated (more mature) cells than pre-OPCs. As used herein, an "oligodendrocyte progenitor cells" or "OPC" refers to a stem cell-derived progenitor cell that expresses the cellular markers OLIG2 and NKX2.2, as well as PDGFRα. An OPC may express additional markers, non-limiting example of which include SOX10 (neural crest marker), OTX2 (anterior neuroectoderm biomarker), FEZF2 (anterior ectoderm biomarker), and/or OLIG1.

The pre-OPCs and OPCs generated by the methods of the disclosure can be further cultured in vitro to generate mature oligodendrocytes (OL). Markers of mature OLs include but are not limited to myelin basic protein (MBP) and O4.

II. Culture Media Components

The method of the disclosure for generating pre-OPCs or OPCs comprise culturing human pluripotent stem cells in a culture media lacking exogenously-added growth factors and comprising specific agonist and/or antagonists of cellular signaling pathways.

As described in Example 1, a culture media comprising a retinoic acid (RA) pathway agonist, an Akt pathway agonist and an mTOR pathway agonist was sufficient to generate OLIG2 and NKX2.2-expressing pre-OPCs in as little as three days. Inclusion of additional agents optimized for expression of other markers, including PDGFRa as a marker of OPC differentiation. In other embodiments, the culture media further comprises at least one additional agent selected from the group consisting of WNT pathway antagonists, SHH pathway agonists, BMP pathway antagonists and PKC pathway antagonists. In one embodiment, the culture media further comprises a WNT pathway antagonist. In one embodiment, the culture media further comprises an SHH pathway agonist. In one embodiment, the culture media further comprises a BMP pathway antagonist. In one embodiment, the culture media further comprises a PKC pathway antagonist. In one embodiment, the culture media further comprises a WNT pathway antagonist and an SHH pathway agonist, wherein the differentiated cells express OTX2 and FEZF2, in addition to OLIG2 and NKX2.2.

In one embodiment, the culture media comprises a retinoic acid (RA) pathway agonist, an Akt pathway agonist, an mTOR pathway agonist, a WNT pathway antagonist, an SHH pathway agonist, a BMP pathway antagonist and a PKC pathway antagonist. In one embodiment, the differentiated cells are OPCs expressing at least OLIG2, NKX2.2 and PDGFRa (and may express additional markers, such as OTX2, FEZF2 and/or OLIG1).

As used herein, an "agonist" of a cellular signaling pathway is intended to refer to an agent that stimulates (upregulates) the cellular signaling pathway. Stimulation of the cellular signaling pathway can be initiated extracellularly, for example by use of an agonist that activates a cell surface receptor involved in the signaling pathway (e.g., the agonist can be a receptor ligand). Additionally or alternatively, stimulation of cellular signaling can be initiated intracellularly, for example by use of a small molecule agonist that interacts intracellularly with a component(s) of the signaling pathway.

As used herein, an "antagonist" of a cellular signaling pathway is intended to refer to an agent that inhibits (downregulates) the cellular signaling pathway. Inhibition of the cellular signaling pathway can be initiated extracellularly, for example by use of an antagonist that blocks a cell surface receptor involved in the signaling pathway. Additionally or alternatively, inhibition of cellular signaling can be initiated intracellularly, for example by use of a small molecule antagonist that interacts intracellularly with a component(s) of the signaling pathway.

Retinoic acid (RA) pathway agonists, Akt pathway agonists, mTOR pathway agonists, WNT pathway antagonists, SHH pathway agonists, BMP pathway antagonists and PKC pathway antagonists are known in the art and commercially available. They are used in the culture media at a concentration effective to achieve the desired outcome, e.g., generation of pre-OPCs and/or OPCs expressing markers of interest. Non-limiting examples of suitable agonist and antagonists agents, and effective concentration ranges, are described further below.

Agonists of the RA pathway include agents, molecules, compounds, or substances capable of stimulation of a retinoic acid receptor (RAR) that is activated by both all-trans retinoic acid and 9-cis retinoic acid. There are three RARs: RAR-alpha, RAR-beta and RAR-gamma, which are encoded by the RARA, RARB, RARG genes, respectively. Different retinoic acid analogs have been synthesized that can activate the retinoic acid pathway. Non-limiting examples of such compounds include TTNPB (agonist of RAR-alpha, beta and gamma), AM 580 (RARalpha agonist), CD 1530 (potent and selective RARgamma agonist), CD 2314 (selective RARbeta agonist), Ch 55 (potent RAR agonist), BMS 753 (RARalpha-selective agonist), Tazarotene (receptor-selective retinoid; binds RAR-beta and -gamma), Isotretinoin (endogenous agonist for retinoic acid receptors; inducer of neuronal differentiation), and AC 261066 (RARβ2 agonist). In some embodiments, the RA signaling pathway agonist is selected from the group consisting of: i) a retinoid compound, ii) a retinoid X receptor (RXR) agonist, and iii) a 25 retinoic acid receptor (RARs) agonist. In particular embodiments, the RA pathway agonist is selected from the group consisting of: retinoic acid, Sr11237, adapalene, EC23, 9-cis retinoic acid, 13-cis retinoic acid, 4-oxo retinoic acid, and All-trans Retinoic Acid (ATRA).

Accordingly, in one embodiment, the RA pathway agonist is selected from the group consisting of TTNPB, AM 580, CD 1530, CD 2314, Ch 55, BMS 753, Tazarotene, Isotretinoin, AC 261066, retinoic acid (RA), Sr11237, adapalene, EC23, 9-cis retinoic acid, 13-cis retinoic acid, 4-oxo retinoic acid, and All-trans Retinoic Acid (ATRA), or combinations thereof. In one embodiment, the RA pathway agonist is present in the culture media at a concentration within a range of 5-500 mM, or 10-100 nM or 25-75 nM. In one embodiment, the RA pathway agonist is TTNPB. In one embodiment, the RA pathway agonist is TTNPB, which is present in the culture media at a concentration within a range of 5-500 nM, or 10-100 nM or 25-75 nM. In one embodiment, the RA pathway agonist is TTNPB, which is present in the culture media at a concentration of 50 nM.

Agonists of the Akt pathway include agents, molecules, compounds, or substances capable of stimulating (activating) the signaling pathway of one or more of the serine/threonine kinase Akt family members, which include Akt1 (also designated PKB or RacPK), Akt2 (also designated PKBβ or RacPK-β) and Akt 3 (also designated PKBγ or thyoma viral proto-oncogene 3). In one embodiment, the Akt pathway agonist is a pan-Akt activator. In one embodiment, the pan Akt activator is SC79. In one embodiment, the Akt pathway agonist is present in the culture media at a concentration within a range of 0.1-10 μM. In one embodiment, the Akt pathway agonist is SC79. In one embodiment, the Akt pathway agonist is SC79, which is present in the culture media at a concentration of 0.1-10 μM, or 0.5-5 μM, or 0.5-2.5 μM or 0.5-1.5 μM. In one embodiment, the Akt pathway agonist is SC79, which is present in the culture media at a concentration of 1 μM.

Agonists of the mTOR (mammalian target of rapamycin) pathway include agents, molecules, compounds, or substances capable of stimulating (activating) signaling through mTOR, a PI3K-related kinase family member which is a core component of the mTORC1 and mTORC2 complexes. In one embodiment, the mTOR pathway agonist is selected from the group consisting of MHY1485, 3BDO, Salidroside, L-Leucine, NV-5138, and combinations thereof. In one embodiment, the mTOR pathway agonist is present in the culture media at a concentration within a range of 0.1-10 μM, or 0.5-5 μM, or 0.5-2.5 μM or 0.5-1.5 μM. In one embodiment, the mTOR pathway agonist is MHY1485. In one embodiment, the mTOR pathway agonist is MHY1485, which is present in the culture media at a concentration of 0.1-10 μM, or 0.5-5 μM or 0.5-2.5 μM or 0.5-1.5 μM. In one embodiment, the mTOR pathway agonist is MHY1485, which is present in the culture media at a concentration of 1 µM.

Antagonists of the WNT pathway include agents, molecules, compounds, or substances capable of inhibiting (downregulating) the canonical Wnt/β-catenin signaling pathway, which biologically is activated by binding of a Wnt-protein ligand to a Frizzled family receptor. In one embodiment, the WNT pathway antagonist is selected from the group consisting of XAV939, ICG001, Capmatinib, endo-IWR-1, IWP-2, IWP-4, MSAB, CCT251545, KY02111, NCB-0846, FH535, LF3, WIKI4, Triptonide, KYA1797K, JW55, JW 67, JW74, Cardionogen 1, NLS-StAx-h, TAK715, PNU 74654, iCRT3, WIF-1, DKK1, and combinations thereof. In one embodiment, the WNT pathway antagonist is present in the culture media at a concentration within a range of 10-500 nM, 50-250 nM or 50-150 nM. In one embodiment, the WNT pathway antagonist is XAV939. In one embodiment, the WNT pathway antagonist is XAV939, which is present in the culture media at a concentration of 10-500 nM, 50-250 nM or 50-150 nM. In one embodiment, the WNT pathway antagonist is XAV939, which is present in the culture media at a concentration of 100 nM.

Agonists of the SHH (sonic hedgehog) pathway include agents, molecules, compounds, or substances capable of stimulating (activating) signaling through the SHH pathway, which biologically involves binding of SHH to the Patched-1 (PTCH1) receptor and transduction through the Smoothened (SMO) transmembrane protein. In one embodiment, the SHH pathway agonist is selected from the group consisting of Purmorphamine, GSA 10, SAG, and combinations thereof. In one embodiment, the SHH pathway agonist is present in the culture media at a concentration within a range of 100-1000 nM, or 250-750 nM or 400-600 nM. In one embodiment, the SHH pathway agonist is Purmorphamine. In one embodiment, the SHH pathway agonist is Purmorphamine, which is present in the culture media at a concentration of 100-1000 nM, or 250-750 nM or 400-600 nM. In one embodiment, the SHH pathway agonist is Purmorphamine, which is present in the culture media at a concentration of 500 nM.

Antagonists of the BMP (bone morphogenetic protein) pathway include agents, molecules, compounds, or substances capable of inhibiting (downregulating) the BMP signaling pathway, which biologically is activated by binding of BMP to a BMP receptor, which are activin receptor-like kinases (ALK) (e.g., type I BMP receptor, including but not limited to ALK2 and ALK3). In one embodiment, the BMP pathway antagonist is selected from the group consisting of LDN193189, DMH1, DMH2, Dorsopmorphin, K02288, LDN214117, LDN212854, folistatin, ML347, Noggin and combinations thereof. In one embodiment, the BMP pathway antagonist is present in the culture media at a concentration within a range of 100-1000 nM, 150-750 nM, 100-500 nM, or 150-350 nM. In one embodiment, the BMP pathway antagonist is LDN193189. In one embodiment, the BMP pathway antagonist is LDN193189, which is present in the culture media at a concentration of 100-1000 nM, 150-750 nM, 100-500 nM, or 150-350 nM. In one embodiment, the BMP pathway antagonist is LDN193189, which is present in the culture media at a concentration of 250 nM.

Antagonists of the PKC (protein kinase C) pathway include agents, molecules, compounds, or substances capable of inhibiting (downregulating) a PKC signaling pathway, which biologically is mediated by a PKC family member. The PKC family of serine/threonine kinases comprises fifteen isozymes, including the "classical" PKC sub-category, which contain the isoforms α, β1, β2 and γ. In one embodiment, the PKC pathway antagonist inhibits the activity of at least one (and in other embodiments, at least two or three) PKC enzyme selected from PKCα, PKCβ1, PKCβ2 and PKCγ. In one embodiment, the PKC pathway antagonist is selected from the group consisting of Go 6983, Sotrastaurin, Enzastaurin, Staurosporine, LY31615, Go 6976, GF 109203X, Ro 31-8220 Mesylate, and combinations thereof. In one embodiment, the PKC pathway antagonist is present in the culture media at a concentration within a range of 10-500 nM, 50-300 nM, 50-150 nM or 75-150 nM. In one embodiment, the PKC pathway antagonist is Go 6983. In one embodiment, the PKC pathway antagonist is Go 6983, which is present in the culture media at a concentration of 10-500 nM, 50-300 nM, 50-150 nM or 75-150 nM. In one embodiment, the PKC pathway antagonist is Go 6983, which is present in the culture media at a concentration of 110 nM.

III. Culture Conditions

In combination with the chemically-defined and optimized culture media described in subsection II above, the methods of generating pre-OPCs and OPCs of the disclosure utilize standard culture conditions established in the art for cell culture. For example, cells can be cultured at 37° C. and under 5% 02 and 5% $CO_2$ conditions. Cells can be cultured in standard culture vessels or plates, such as 96-well plates. In certain embodiments, the starting pluripotent stem cells are adhered to plates, preferably coated with an extracellular matrix material such as vitronectin. In one embodiment, the stem cells are cultured on a vitronectin coated culture surface (e.g., vitronectin coated 96-well plates).

Pluripotent stem cells can be cultured in commercially-available media prior to differentiation. For example, stem cells can be cultured for at least one day in Essential 8 Flex media (Thermo Fisher #A2858501) prior to the start of the differentiation protocol. In a non-limiting exemplary embodiment, stem cells are passaged onto vitronectin (Thermo Fisher #A14700) coated 96-well plates at 150,000 cells/cm2 density and cultured for one day in Essential 8 Flex media prior to differentiation.

To begin the differentiation protocol, the media the stem cells are being cultured in is changed to a basal differentiation media that has been supplemented with signaling pathway agonists and/or antagonists as described above in subsection II. A basal differentiation media can include, for example, a commercially-available base supplemented with additional standard culture media components needed to maintain cell viability and growth, but lacking serum (the basal differentiation media is a serum-free media) or any other exogenously-added growth factors, such as FGF2, PDGF, IGF or HGF. In a non-limiting exemplary embodiment, a basal differentiation media contains 1×IMDM (Thermo Fisher #12440046), 1×F12 (Thermo Fisher #11765047), poly(vinyl alcohol) (Sigma #p8136) at 1 mg/ml, chemically defined lipid concentrate (Thermo Fisher #11905031) at 1%, 1-thioglycerol (Sigma #M6145) at 450 uM, Insulin (Sigma #11376497001) at 0.7 ug/ml and transferrin (Sigma #10652202001) at 15 ug/ml.

The culture media typically is changed regularly to fresh media. For example, in one embodiment, media is changed every 24 hours.

To generate pre-OPCs and/or OPCs, the stem cells are cultured in the optimized culture media for sufficient time for cellular differentiation and expression of pre-OPC- or OPC-associated markers. As described in the Examples, it has been discovered that culture of the stem cells in the optimized culture media for as little as 72 hours (3 days) was sufficient for pre-OPC and OPC differentiation. Accordingly, in one embodiment, cells are cultured for at least 72 hours. In other embodiments, cell are cultured for at least 60, 64, 68, 72, 76, 80, 84, 88, 92 or 96 hours. In other embodiments, cells are cultured for at least 2.5, 3, 3.5, 4, 4.5 or 5 days.

IV. Uses

The methods and compositions of the disclosure for generating pre-OPCs and OPCs allow for efficient and robust availability of these cell populations for a variety of uses. For example, the methods and compositions can be used in the study of oligodendrocyte development and biology to assist in the understanding of oligodendrocyte-related diseases and disorders. For example, the pre-OPCs and/or OPCs generated using the methods of the disclosure can be further purified according to methods established in the art using agents that bind to surface markers expressed on the cells. Accordingly, in one embodiment, the disclosure provides a method of isolating pre-oligodendrocyte progenitor cells (pre-OPCs) or oligodendrocyte progenitor cells (OPCs), the method comprising:

contacting OLIG2-expressing pre-OPCs or OPCs generated by a method of the disclosure with at least one binding agent that binds to a cell surface marker expressed by the pre-OPCs or OPCs; and isolating cells that bind to the binding agent to thereby isolate the pre-OPCs or OPCs.

In one embodiment, the binding agent is an antibody, e.g., a monoclonal antibody (mAb) that binds to the cell surface marker. Non-limiting examples of suitable OPC cell surface markers include PDGFRα, O4 and A2B5. Cells that bind the antibody can be isolated by methods known in the art, including but not limited to fluorescent activated cell-sorting (FACS) and magnetic activated cell sorting (MACS).

Progenitors of the oligodendrocyte lineage also are contemplated for use in the treatment of various oligodendrocyte-related diseases and disorders, through delivery of the cells to a subject having the disease or disorder. Examples of oligodendrocyte-related diseases and disorders include, but are not limited to, multiple sclerosis (MS), progressive multifocal leukoencephalopathy, periventricular leukomalacia, certain leukodystrophies and amyotrophic lateral sclerosis (ALS).

V. Compositions

In other aspects, the disclosure provides compositions related to the methods of generating pre-OPCs and OPCs, including culture media and cell cultures, as well as isolated progenitor cells and cell populations.

In one aspect, the disclosure provides a culture media for obtaining pre-OPCs or OPCs lacking exogenously-added growth factors and comprising a retinoic acid (RA) pathway agonist, an Akt pathway agonist and an mTOR pathway agonist. In one embodiment, the culture media further comprises a WNT pathway antagonist. In one embodiment, the culture media further comprises an SHH pathway agonist. In one embodiment, the culture media further comprises a WNT pathway antagonist and an SHH pathway agonist. In one embodiment, the culture media further comprises a BMP pathway antagonist. In one embodiment, the culture media further comprises a PKC pathway antagonist. In one embodiment, the culture media further comprises a BMP pathway antagonist and a PKC pathway antagonist. In one embodiment, the culture media comprises a retinoic acid (RA) pathway agonist, an Akt pathway agonist, an mTOR pathway agonist, a WNT pathway antagonist, an SHH pathway agonist, a BMP pathway antagonist and a PKC pathway antagonist.

In one aspect, the disclosure provides an isolated cell culture of pre-OPCs or OPCs, the culture comprising: OLIG2-expressing pre-OPCs or OPCs cultured in a culture media comprising a retinoic acid (RA) pathway agonist, an Akt pathway agonist and an mTOR pathway agonist and lacking exogenously-added growth factors. In various embodiments, the culture media can also comprise a WNT pathway antagonist, an SHH pathway agonist, a BMP pathway antagonist and/or a PKC pathway antagonist. In one embodiment, the pre-OPCs or OPCs also express NKX2.2. In other embodiments, the pre-OPCs or OPCs also express OTX2 and FEZF2. In one embodiment, the pre-OPCs or OPCs are attached to vitronectin-coated plates.

In another aspect, the disclosure provides a pre-oligodendrocyte progenitor cell (pre-OPC) or an oligodendrocyte progenitor cell (OPC) generated by a differentiation method of the disclosure. In one embodiment, the disclosure provides a composition comprising a non-native pre-OPC or OPC wherein the pre-OPC or OPC expresses OLIG2, NKX2-2, OTX2 and FEZF2 and lacks expression of NESTIN. In another embodiment, the disclosure provides an isolated cell population of pre-OPCs or OPCs comprising at least $1 \times 10^6$ OLIG2 and NKX2.2-expressing pre-OPCs or OPCs, wherein the cell population lacks NESTIN-expressing neural stem cells. In other embodiments, the cell population comprises at least $5 \times 10^6$, $1 \times 10^7$, $5 \times 10^7$, $1 \times 10^8$, $5 \times 10^8$ or $1 \times 10^9$ OLIG2 and NKX2.2-expressing pre-OPCs or OPCs. In on embodiment of the isolated cell population, the pre-OPCs or OPCs are bound with at least one antibody that binds at least one cell surface marker expressed by the pre-OPCs or OPCs. Non-limiting examples of suitable OPC cell surface markers include PDGFRa, O4 and A2B5.

The present invention is further illustrated by the following examples, which should not be construed as further limiting. The contents of figures and all references, patents and published patent applications cited throughout this application are expressly incorporated herein by reference.

EXAMPLES

Example 1: Culture Protocol Development for Generation of Stem Cell-Derived Oligodendrocyte Progenitors In this example, a culture media recipe for generation of oligodendrocyte progenitors was developed that can guide human pluripotent stem cells to differentiate to oligodendrocyte progenitors expressing NKX2-2 and OLIG2 after 3 days in culture. These cells can be further differentiated to mature oligodendrocytes.

This example utilizes a method of High-Dimensional Design of Experiments (HD-DoE), as previously described in Bukys et al. (2020) *Iscience* 23:101346. The method employs computerized design geometries to simultaneously test multiple process inputs and offers mathematical modeling of a deep effector/response space. The method allows for finding combinatorial signaling inputs that control a complex process, such as during cell differentiation. It allows testing of multiple plausible critical process parameters, as such parameters impact output responses, such as gene expression. Because gene expression provides hallmark features of the phenotype of, for example, a human cell, the method can be applied to identify, and understand, which signaling pathways control cell fate. In the current example, the HD-DOE method was applied with the intent to find conditions for induction of oligodendrocyte progenitor-expressed genes, directly from the pluripotent stem cell state.

Specifically, to develop a novel method to generate oligodendrocytes, the impact of agonists and antagonists of multiple signaling pathways (herein called effectors) were tested on expression of two sets of 53 pre-selected genes after a 3-day treatment. These effectors are small molecules that are commonly used during stepwise differentiation of stem cells to specific fates. Choice of the effectors were based on current literature on neural induction in anterior ectoderm and differentiation of stem cells to oligodendrocytes.

HD-DoE #1

To test the effectors, experiments with at least 8 factors were designed that can assess the response of cells to 48 or more different combinations of effectors in a range of concentrations. To analyze the models, we focused on expression of genes expressed during early development of anterior neuroectoderm and oligodendrocytes including NKX2-2, OLIG2, OLIG1, and PDGFRA. The impact of each effector on gene expression level is defined by a parameter called factor contribution that is calculated for each effector during the modeling.

As shown in the results summarized in FIG. 1, one model specifically showed promising results on upregulation of NKX2-2 and OLIG2 genes when optimized for maximum expression of NKX2-2 at 12480.6. This model tested 8 factors: PD0325901, MK2206, TTNPB, SC79, MHY1485, ZM336372, AGN193109 and AZD3147.

Out of the eight factors tested, three of them, namely TTNPB (agonist of retinoic acid pathway), SC79 (agonist of Akt signaling pathway) and MHY1485 (agonist of mTOR signaling pathway), had significant positive effect on expression of targeted genes, with TTNPB having the most impact with factor contribution of 31.3 and MHY1485 with factor contribution of 13.8 and SC79 at 1.47. These factors could bring up expression of NKX2-2 and OLIG2 significantly. OLIG1 and PDGFRA had average expression levels (129.9 and 346.45 respectively) which is compatible with the pattern of gene expression during oligodendrocyte differentiation.

As shown in the results summarized in FIG. 2, normalized expression of PDGFRA in this model could reach up to 832.9 which was the highest expression level out of all models and therefore, the model was also optimized for maximum expression of PDGFRA. This setting showed that TTNPB (agonist of retinoic acid pathway) and MHY1485 (agonist of mTOR signaling pathway) also have a positive effect on upregulation of PGFRA with factor contribution of 49.01 and 13.4, respectively. It was also observed that PD0325901 can have a significant positive effect on this gene with factor contribution of 30.6. Because of low factor contribution of ZM336372 (<1), this factor was not included in the recipe. In this condition, OLIG1 had average expression level at 228.36 similar to conditions of optimization of NKX2-2. One difference in this condition was downregulation of OLIG2 gene from 1049.4 at previous condition to 241.9.

As shown in the results summarized in FIG. 3, out of effectors with positive contribution to expression levels of NKX2-2, OLIG2 or PDGFRA, two factors were negatively impacting NKX2-2 and OLIG2 expression levels. Thus, these two factors, PD0325901 and ZM336372, were eliminated from list of candidates for the recipe of oligodendrocyte differentiation.

Thus, this first HD-DoE screening identified a culture media lacking exogenously-added growth factors and comprising an agonist of retinoic acid pathway, an agonist of Akt signaling pathway and an agonist of mTOR signaling pathway as sufficient to lead to the generation of OLIG2-expressing OPCs from pluripotent stem cells after 3 days (72 hours) of culture.

HD-DoE #2

To further enhance the conditions for oligodendrocyte differentiation from pluripotency, we performed an additional HD-DoE experiment. We obtained additional gene regulatory models that were used for preparation of a differentiation protocol. The basis of this was a 13-factor HD-DoE experiment with focus on initiation of differentiation of cells toward anterior neuroectoderm. In this model, we focused on expression of FEZF2 and OTX2.

As shown in the results summarized in FIG. 4, the model was optimized for highest expression of OTX2 at 12755.9. According to the model of high expression of OTX2, seven effectors had positive contribution including MK2206, PD0325901, CHIR99021, LDN193189, Go6983, PD173074 and BLU9931 with highest factor contribution of 22.2 for MK2206 and lowest factor contribution of 1.7 for PD173074 and BLU9931.

As shown in the results summarized in FIG. 5, the model was optimized for highest expression of FEZF2 at 4466. When the model was optimized for maximum expression level of FEZF2, three effectors including LDN193189 with factor contribution of 19.5, PD0325901 with factor contribution of 14.6 and MK2206 with factor contribution of 12.3 were common with previous condition and three new effectors including purmorphamine-500 nM, XAV939 and SC79 were introduced.

Figure 6:
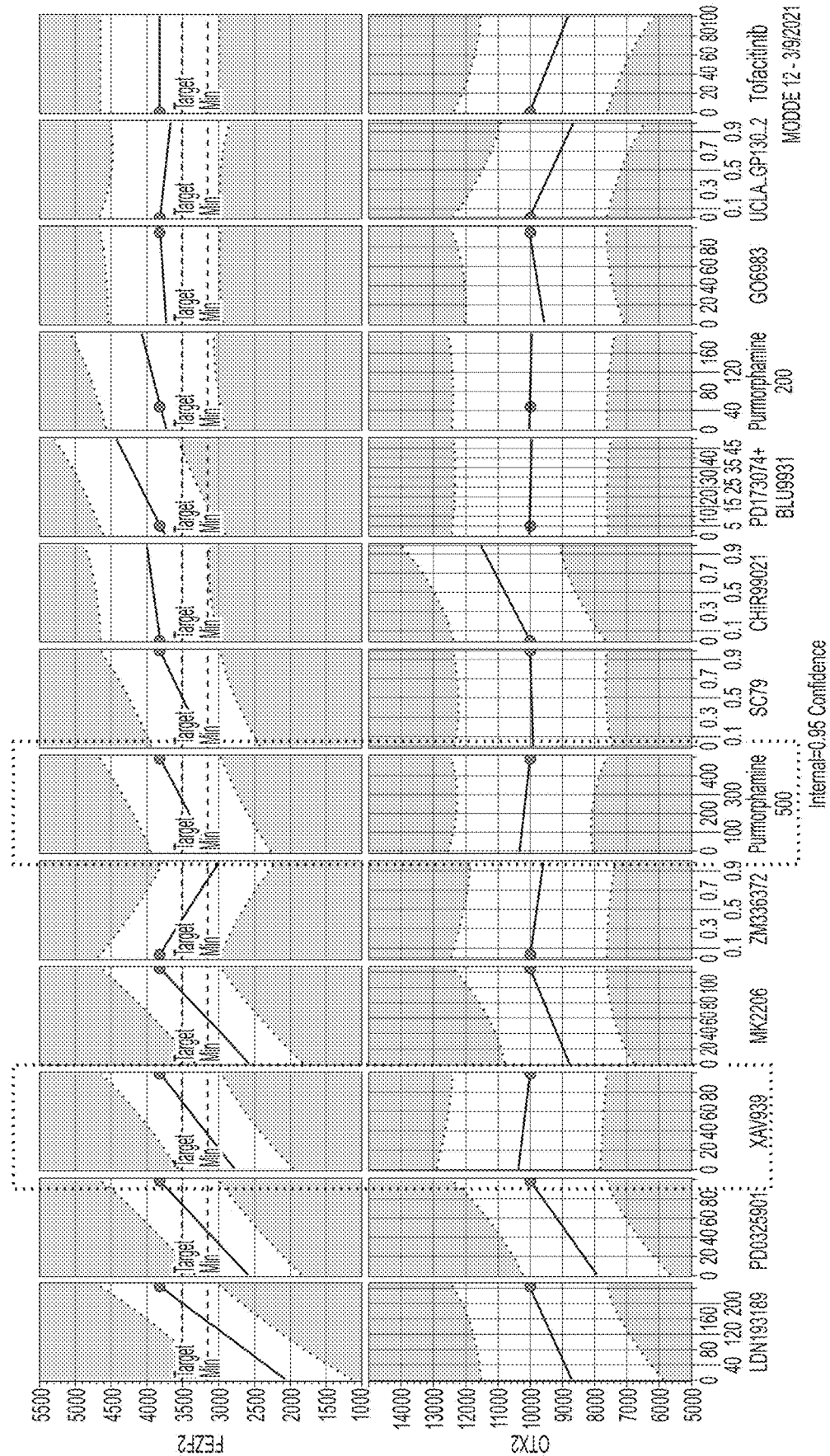
FIG. 6 shows the dynamic profile of expression level of OTX2 and FEZF2 relative to the concentration of 13 factors tested in this model. XAV939 and Purmorphamine-500 nM have a significant positive impact on the expression of FEZF2 and no significant negative impact on the expression of OTX2.

As shown in the results summarized in FIG. 6, to fine-tune the recipe and find the optimum combination of factors for high expression of both OTX2 and FEZF2, dynamic profiling analysis was done. According to this analysis, XAV939 (inhibitor of WNT signaling pathway) and Purmorphamine (agonist of SHH signaling pathway and known for ventralizing the cells during development of regions of the brain) had significant positive effects on expression of FEZF2 and no negative impact on expression level of OTX2. Therefore, these two factors were added to the optimized culture recipe.

In addition to inclusion of factors that promoted expression of OPC-associated surface markers, certain factors that inhibited expression of such markers were eliminated from the optimized culture recipe. CHIR99021, which is the agonist of WNT signaling pathway, was eliminated. MK2206 and PD0325901 were also eliminated, since according to the 8-factor model, they had negative effect on expression of oligodendrocyte genes. PD173074 and BLU9931 were also eliminated because of low factor contribution of 1.7.

Summary

Considering both models, culture conditions that maximized differentiation of human induced pluripotent stem cells to cells having oligodendrocyte progenitor cell (OPC) identity, leading to elevated expression of OTX2, FEZF2, NKX2-2 and OLIG2, included the following effector inputs: TTNPB (RA pathway agonist), SC79 (Akt pathway agonist), MHY1485 (mTOR pathway agonist), Purmorphamine (SHH pathway agonist), XAV939 (WNT pathway antagonist), LDN193189 (BMP pathway antagonist) and Go6983 (PKC pathway antagonist).

Example 2: Factor Criticality Analysis of OPC-Inducing Culture Conditions

To assess the factor criticality of each component in the optimized culture media described in Example 1, we performed in-silico prediction analysis of the outcome under conditions in which individual effectors was eliminated, while keeping others present. To do this, we used dynamic profile analysis at setpoint, while comparing the expression level of genes of interest in absence of each factor. Since expression of genes of interest reveal whether the desired outcome is reachable, this factor criticality analysis revealed the extent of importance of each input effector.

Figure 7A:
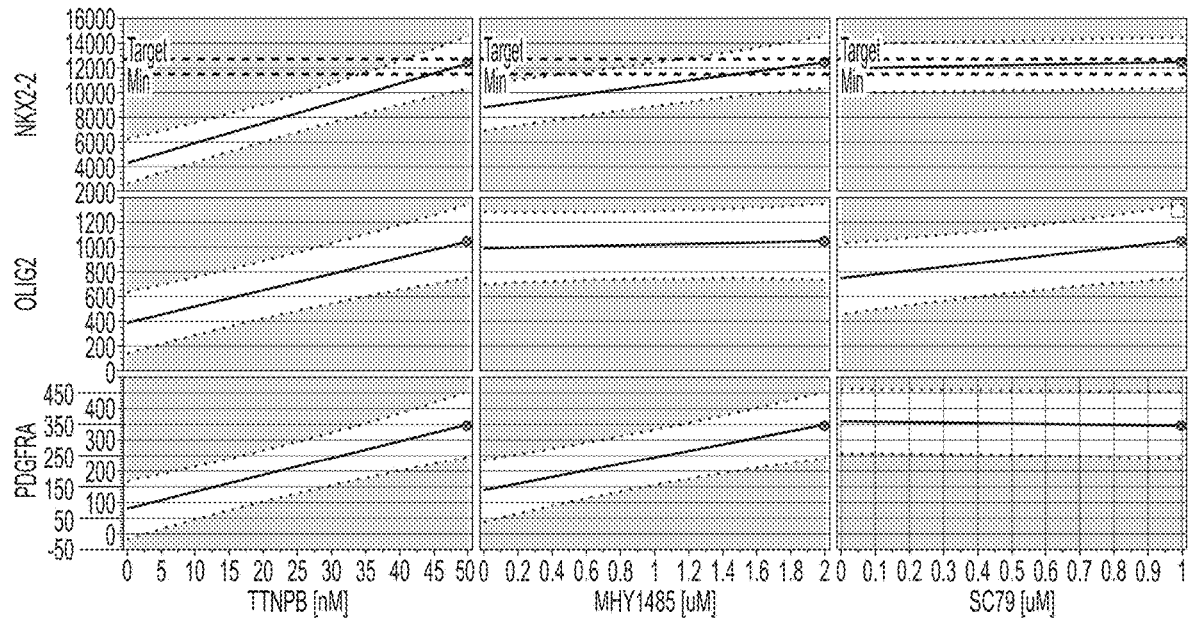
FIG. 7A-D shows the dynamic profile analysis of the elimination process in an 8-factor modeling experiment and its effect on expression of NKX2-2, OLIG2 and PDGFRA.
Figure 7B:
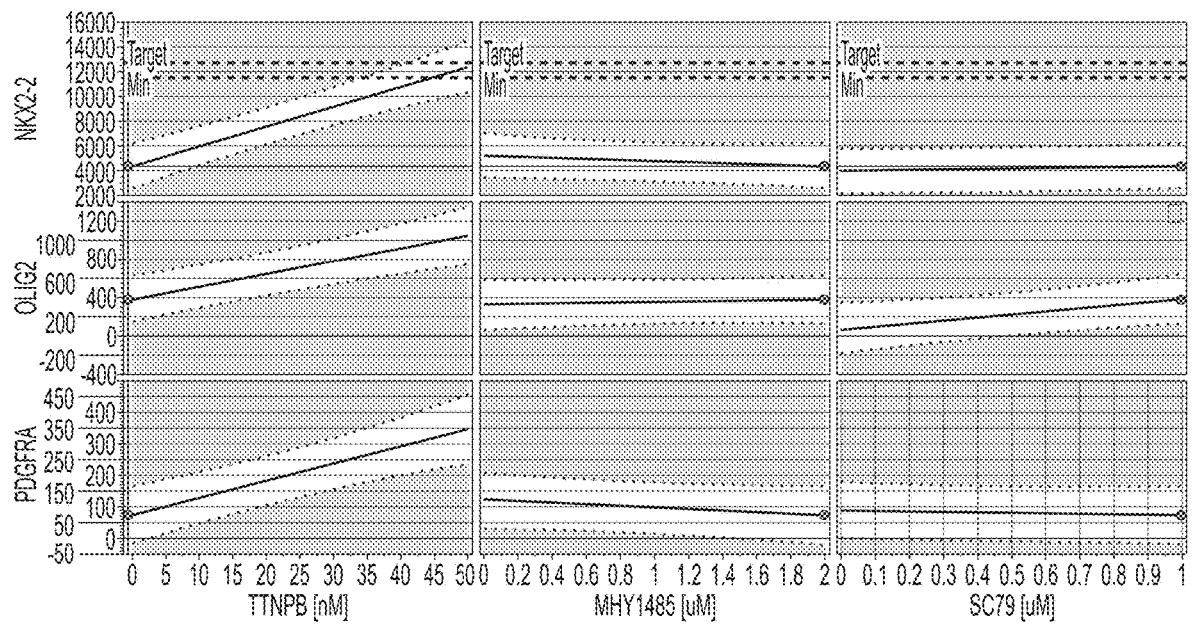
Figure 7C:
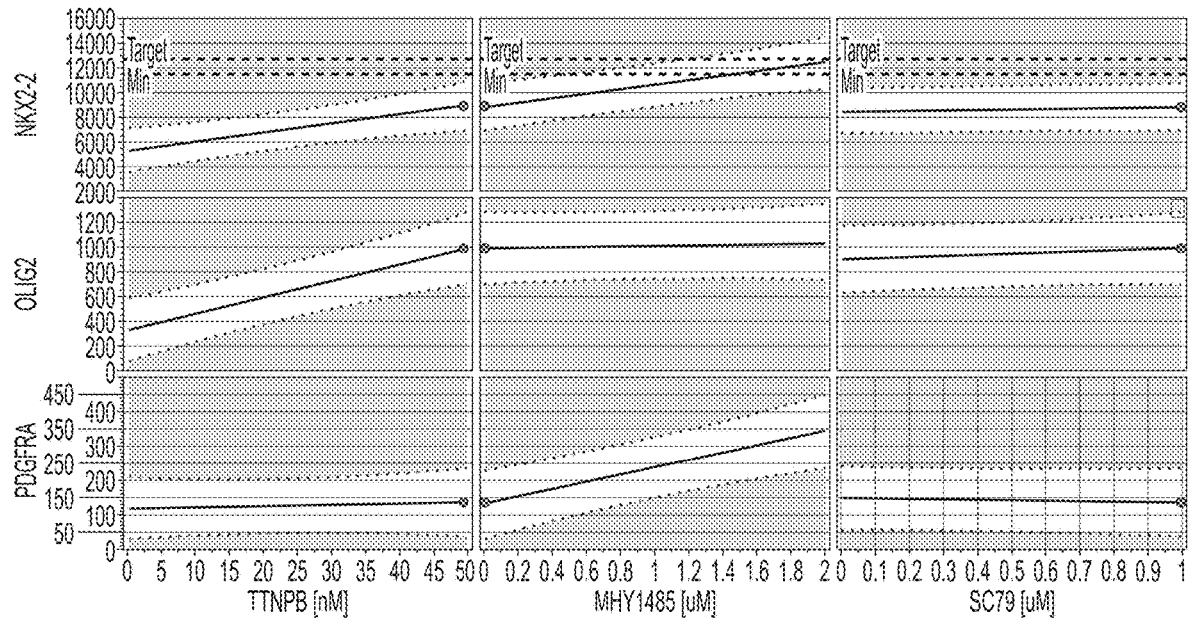
Figure 7D:
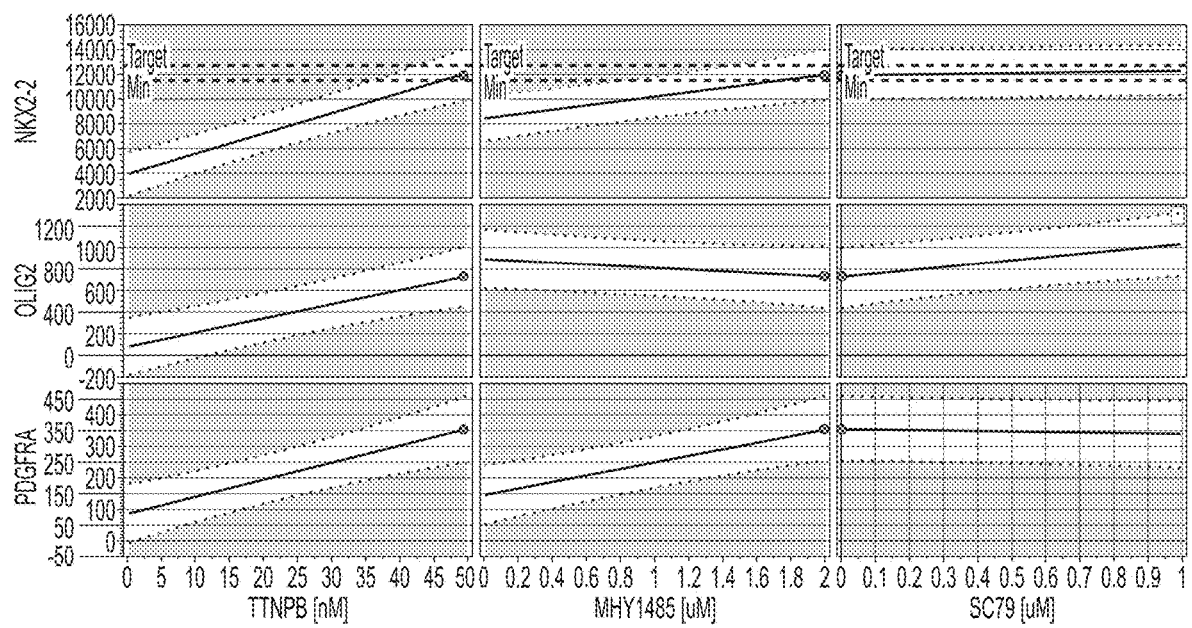
Figure 8A:
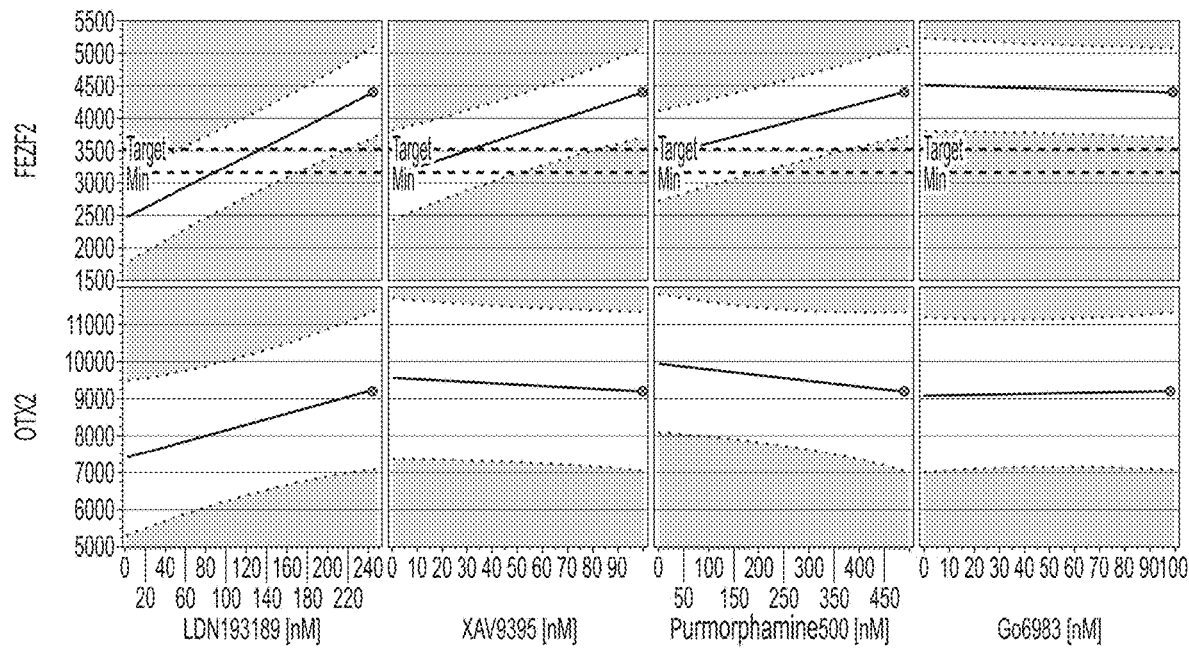
FIG. 8A-D shows the dynamic profile analysis of the elimination process in a 13-factor modeling experiment and its effect on expression of FEZF2 and OTX2.
Figure 8B:
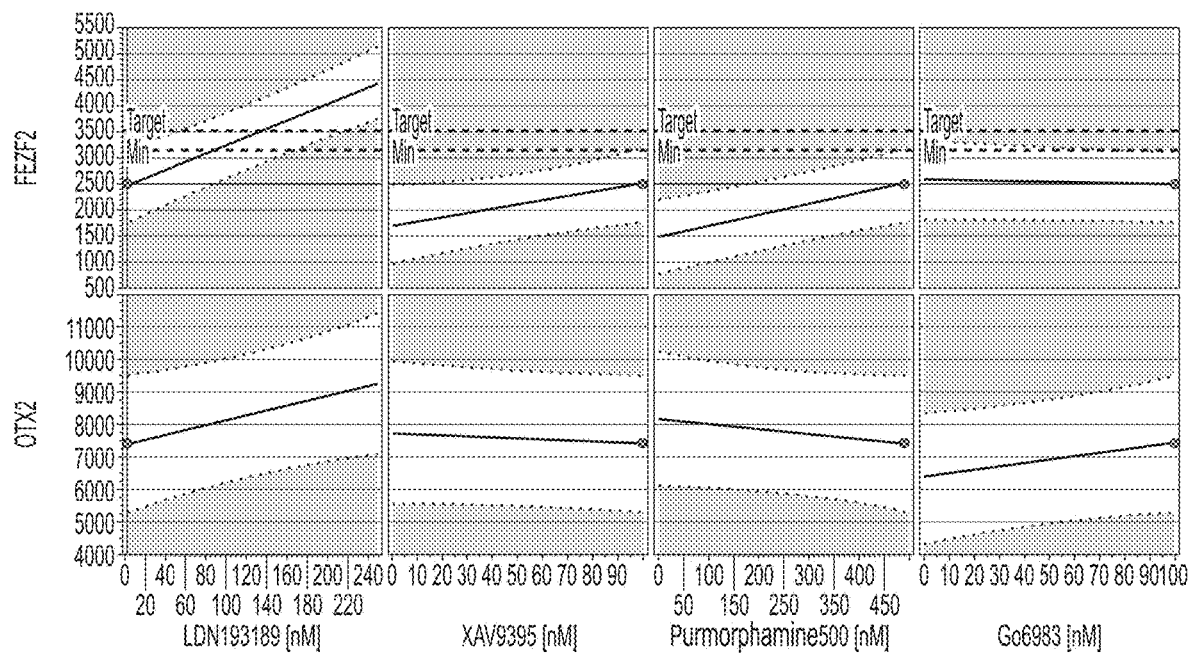
Figure 8C:
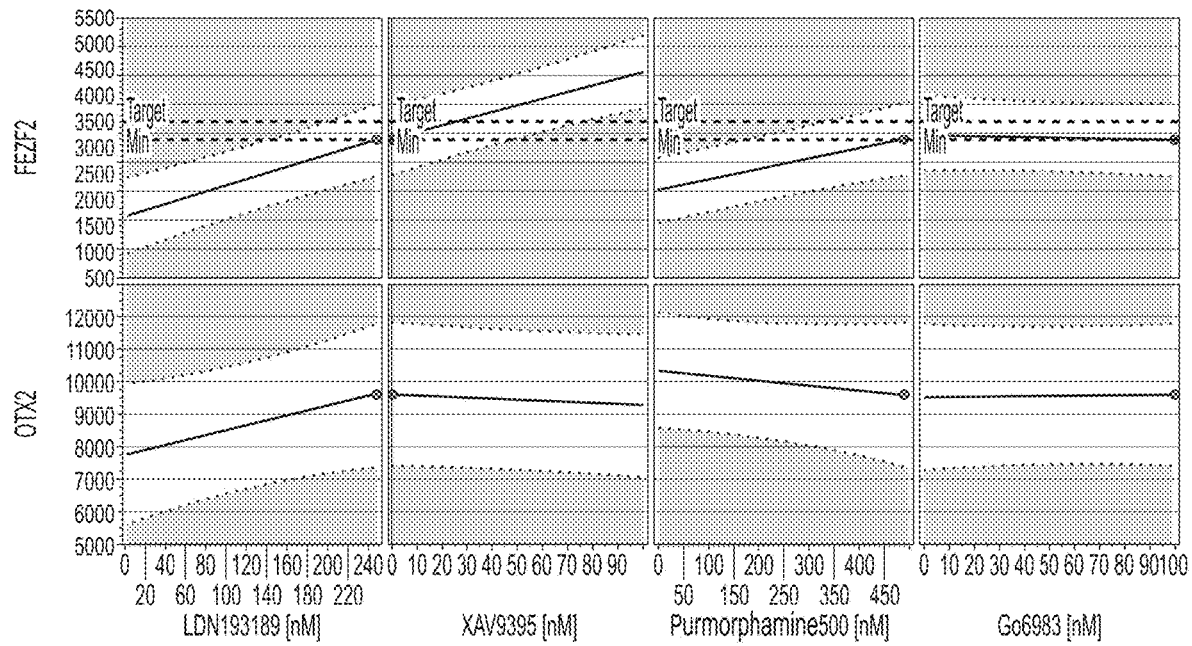
Figure 8D:
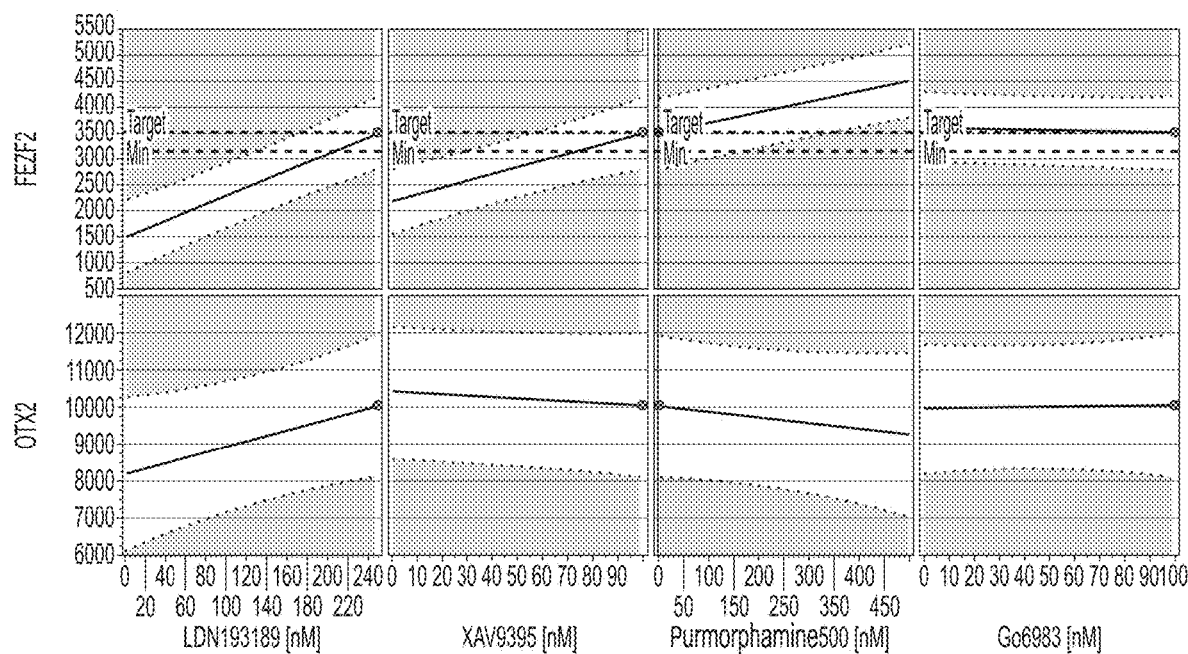

FIG. 7A-D summarize the results for the factor criticality analysis of the effectors TTNPB (RA pathway agonist), SC79 (Akt pathway agonist) and MHY1485 (mTOR pathway agonist). FIG. 7A shows the expression level of the OPC genes of interest in presence of TTNPB, MHY1485 and SC79 when the model is otherwise optimized for maximum expression of NKX2-2. As shown in FIG. 7B, upon removal of TTNPB, the predicted expression levels of NKX2-2, OLIG2 and PDGFRA dropped significantly from more than 12000 to 4500 for NKX2-2, 1000 to 400 for OLIG2 and 350 to less than 100 for PDGFRA. This outcome signifies a significant deleterious effect on expression of all the desired markers when the RA pathway agonist is removed. As shown in FIG. 7C, when MHY1485 was removed, again expression levels decreased, however, not as drastically as previous condition. As shown in FIG. 7D, when SC79 was removed, only a small shift in the plots was observed, which suggests this factor is less critical than TTNPB and MHY1485 for attaining maximal OPC marker induction.

FIG. 8A-D summarize the results for the factor criticality analysis of the effectors Purmorphamine (SHH pathway agonist), XAV939 (WNT pathway antagonist), LDN193189 (BMP pathway antagonist) and Go6983 (PKC pathway antagonist). To attain the desired patterning of the oligodendrocyte population to anterior region of the brain, these additional factor inputs were queried, such as FEZF2 and OTX2. Expression levels of FEZF2 and OTX2 were examined in absence of either LDN193189, XAV, Purmorphamine or Go6983, when the model was optimized for maximum expression of FEZF2. The most significant change was observed in absence of LDN193189 which led to almost 50% reduction in expression of FEZF2 (from 4500 to 2500). Expression of OTX2 was also reduced from 9000 to 7000, which was the lowest in all four elimination processes. When XAV939 and Purmorphamine were removed, expression level of FEZF2 decreased to 3000 and 3500 respectively, while expression of OTX2 was only slightly higher in both cases. When Go6983 was removed, we did not observe any significant changes in the expression level of genes of interest, therefore suggesting G06983 being optional related to control of FEZF2 and OTX2.

Example 3: Immunocytochemistry Validation of Stem Cell-Derived OPCs

Figure 9:
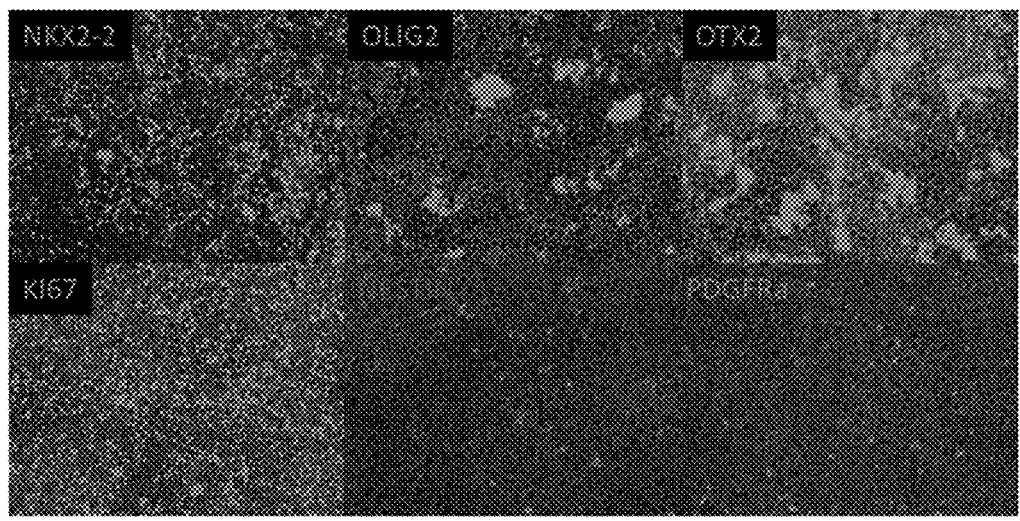
FIG. 9 shows photographs of images of cells cultured in the optimized OPC differentiation media after three days. Cells were stained with oligodendrocyte and neural biomarkers. Cells express anterior neuroectoderm biomarkers including OTX2 and NKX2-2 along with OPC specific biomarker OLIG2. NESTIN and PDGFRα, which are neuronal and late OPC biomarkers respectively, are not present. Expression of KI67 shows the proliferative state of precursor cells.

To further validate the optimized culture media described in Example 1, cells were cultured in the optimized media for 3 days and immunocytochemistry was used to assess expression of biomarkers of anterior neuroectoderm and oligodendrocyte progenitors. Biomarkers included OTX2 and oligodendrocyte precursor biomarkers including NKX2-2, OLIG2 and PDGF. Nestin, an early neuronal marker was used to distinguish between neural stem cells and oligodendrocyte progenitors. Ki67 was also used to confirm the proliferation of cells after induction. Representative immunohistochemistry results are shown in FIG. 9. These immunocytochemistry images confirmed that most of the cells expressed OTX2. However, there was no trace of the neuronal biomarker Nestin detected, confirming that the differentiated OPC population lacks neural stem cells. Expression of OLIG2 and NKX2-2 was also observed in more than 90% of the cells, thereby confirming the oligodendrocyte lineage of the cells. None of the cells expressed PDGFR which was expected since this gene is expressed at later stages of differentiation of oligodendrocytes.

Example 4: RNA-Seq Validation of Stem Cell-Derived Pre-OPC

Figure 10A:
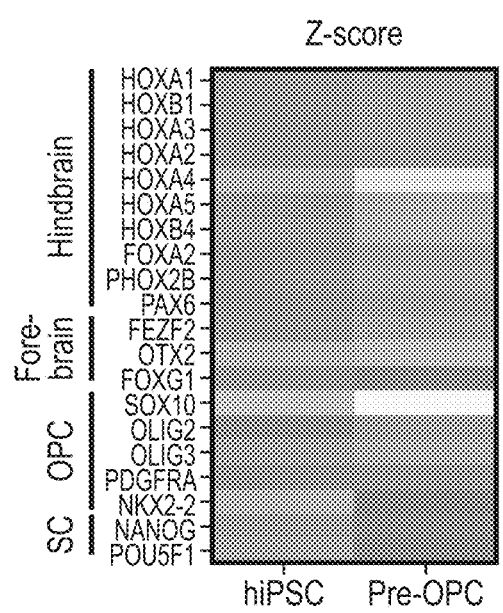
FIG. 10A-B shows RNA-seq data of cells cultured in optimized OPC differentiation media after three days. Expression level of stem cell genes NANOG and POU5F1 were decreased while genes involved in early development of brain regions and oligodendrocyte lineage were elevated.
Figure 10B:
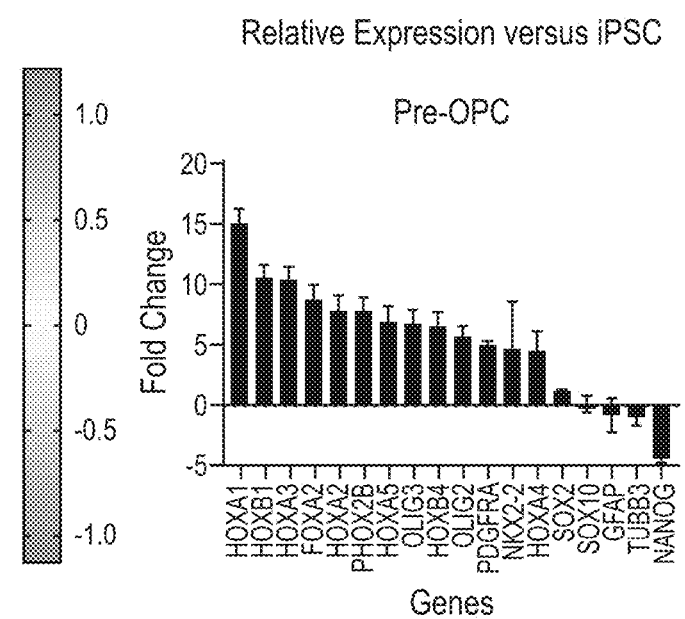

RNA sequencing was used to obtain a gene profile of cells cultured in the differentiation media detailed in Examples 1 and 2. hiPSCs were cultured for 3 days in the media and RNA from the generated cells was sequenced by standard RNA-seq analysis. The results in FIG. 10A show normalized expression levels of selected genes representative of various regions of the brain, early oligodendrocyte identity (NKX2-2, OLIG2, PDGFRa) and stem cell state (NANOG, POU5F1) in three replicates at day 0 and day 3. The results demonstrated that the level of stem cell genes decreased in pre-OPC cells while the level of oligodendrocyte genes increased, which validated the differentiation of hiPSCs to oligodendrocyte lineage using the differentiation media. The results of FIG. 10B show differential expression and fold change of the selected genes, with HOXA1 at highest level (15) and OLIG2, NKX2-2 and PDGFRa at 5. This data demonstrates the ability of developed recipe as a stage 1 media in directing the cells toward oligodendrocyte identity.

EQUIVALENTS

Those skilled in the art will recognize, or be able to ascertain using no more than routine experimentation, many equivalents of the specific embodiments of the invention described herein. Such equivalents are intended to be encompassed by the following claims

The invention claimed is:

1. A culture media comprising the retinoic acid (RA) pathway agonist TTNPB, the Akt pathway agonist SC79, the mTOR pathway agonist MHY1485, the WNT pathway antagonist XAV939 and the SHH pathway agonist Purmorphamine and lacking exogenously-added growth factors and serum.

2. The culture media of claim 1, which comprises 50 nM TTNPB, 1 mM SC79 and 1 mM MHY1485.

3. The culture media of claim 1, which further comprises the BMP pathway antagonist LDN193189 and the PKC pathway antagonist Go6983.

4. The culture media of claim 3, which comprises 50 nM TTNPB, 1 mM SC79, 1 mM MHY1485, 100 nM XAV939, 500 nM Purmorphamine, 250 nM LDN193189 and 110 nM Go6983.

* * * * *